US007141600B2

(12) United States Patent  
Guy et al.

(10) Patent No.: US 7,141,600 B2
(45) Date of Patent: Nov. 28, 2006

(54) SMALL MOLECULE INHIBITION OF A PDZ-DOMAIN INTERACTION

(75) Inventors: R. Kiplin Guy, Concord, CA (US); Irwin D. Kuntz, Greenbrae, CA (US); Jose Haresco, San Francisco, CA (US); Naoaki Fujii, South San Francisco, CA (US); Kathleen P. Novak, Watham, MA (US); David Stokoe, San Francisco, CA (US); Biao He, San Mateo, CA (US); Liang You, San Francisco, CA (US); Zhidong Xu, San Francisco, CA (US); David M. Jablons, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 10/826,175

(22) Filed: Apr. 15, 2004

(65) Prior Publication Data

US 2005/0043385 A1 Feb. 24, 2005

Related U.S. Application Data

(60) Provisional application No. 60/463,198, filed on Apr. 15, 2003.

(51) Int. Cl.
*A61K 31/404* (2006.01)
*C07D 209/12* (2006.01)
*C07D 209/30* (2006.01)
*C07D 209/04* (2006.01)

(52) U.S. Cl. .................. 514/415; 548/491; 548/490; 548/469; 548/465

(58) Field of Classification Search ............. 548/491, 548/490, 469, 465; 514/415
See application file for complete search history.

(56) References Cited

U.S. PATENT DOCUMENTS

| 5,260,322 | A | 11/1993 | Nakasima et al. |
| 5,852,046 | A | 12/1998 | Lang et al. |
| 6,069,156 | A | 5/2000 | Oku et al. |
| 6,265,547 | B1 | 7/2001 | Yue et al. |
| 6,358,992 | B1 | 3/2002 | Pamukcu et al. |
| 2002/0137129 | A1 | 9/2002 | Barnes et al. |

FOREIGN PATENT DOCUMENTS

| EP | 0624628 A1 | 11/1994 |
| EP | 0839573 A1 | 2/1995 |
| JP | 05-281721 | 10/1993 |
| JP | 11-180801 | 7/1999 |
| WO | WO 97/48697 | 12/1997 |

OTHER PUBLICATIONS

Xing, et al. "Design of Cancer-Specific Antitumor Agents Based on Aziridinylcyclopent[b]indoloquinones", J. Med. Chem. 43(3), 457-66 (2000).*

Fuji et al., "Targeting PDZ-domain by rationally designed non-peptide small molecules", poster presentation at a conference of the American Society of Cell Biology, Dec. 2002.

Harris et al., "Mechanism and role of PDZ domains in signaling complex assembly", Journal of Cell Science, 2001, vol. 114 pp. 3219-3231.

Lee et al., "Multi-PDZ domain protein MUPP1 is a Cellular Target . . . ", Journal of Virology, 2000, vol. 74 pp. 9680-9693.

Novak et al., Investigation of the PDZ domain ligand binding site using chemically modified peptides, 2002, Bioorganic & Medicinal Chemistry Letters, vol. 12 pp. 2471-2474.

Novak et al., Fishing-up PDZ by tagged-FJ-3; slide presented at a conference of the American Chemical Society, Mar. 2003.

Novak et al., "Small molecule inhibition of a PDZ domain interaction", poster presented at a conference of the American Society of Biochemistry and Molecular Biology, Apr. 15, 2003.

(Continued)

*Primary Examiner*—Kamal A. Saeed
*Assistant Examiner*—Michael P. Barker
(74) *Attorney, Agent, or Firm*—Townsend and Townsend and Crew LLP.

(57) ABSTRACT

Novel compounds that have been found effective in inhibiting PDZ domain interactions, and particularly interactions of PDZ domains in MAGIs with the oncogenic (tumor suppressor) protein PTEN and interactions between the PDZ domain in the Dishevelled (Dvl) protein and other proteins such as the Frizzled (Fz) protein, have the general formula

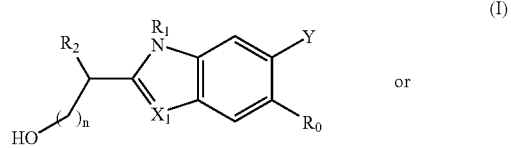

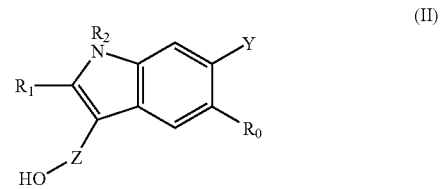

The invention also includes combinatorial libraries, arrays and methods for screening and studying proteins using such compounds.

Compounds of the invention have produced apoptosis in certain cell lines that overexpress the Dishevelled protein (Dvl); inhibiting Wnt signaling.

18 Claims, 4 Drawing Sheets

OTHER PUBLICATIONS

Ponting et al., "PDZ domains: targeting signalling molecules to sub-membranous sites", 1997, BioEssays vol. 19 pp. 469-479.

Shibata et al., "EBP50, a beta-catenin-associating protein, enhances Wnt signaling . . . ", 2003, Heptatology, vol. 38 pp. 178-186.

Stemmer-Rachamimov et al., "NHE-RF, A Merlin-interacting protein, is primarily expressed in . . . ", 2001, American Journal of Pathology, vol. 158 pp. 57-62.

Uematsu et al., "Wnt pathway Activation in mesothelioma", 2003, Cancer Research vol. 63 pp. 4547-4551.

Uematsu et al., Activation of the Wnt pathway in non small cell lung cancer, 2003, Oncogene, vol. 22 pp. 7218-7221.

Wong et al., Direct bonding of the PDZ domain of Dishevelled to a conserved internal sequence in the C-terminal region of Frizzle, 2003, vol. 12 pp. 1251-1260.

Hulme et al., The Synthesis and biological evaluation of a novel series of indole PDE4 inhibitors, 1998, Bioorganic & Medicinal Chemistry Letters, vol. 8 pp. 1867-1872.

* cited by examiner

SEQUENCE LISTING

<160> NUMBER OF SEQ ID NOS: 5

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:fluorescein
      labeled carboxy terminal sequence of PTEN
      fluorescence polarization competion assay probe
<220> FEATURE:
<221> NAME/KEY: MOD_RES
<222> LOCATION: (1)
<223> OTHER INFORMATION: Xaa = Pro modified by OregonGreen

<400> SEQUENCE: 1

Xaa Phe Asp Glu Asp Gln His Thr Gln Ile Thr Lys Val
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:highest
      affinity peptide sequence for MAGI-3 PDZ2
      fluorescence polarization competion assay positive
      control

<400> SEQUENCE: 2

Pro Phe Asp Glu Asp Gln His Thr Gln Ile Thr Trp Val
 1               5                  10

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence:fluorescence
      polarization competion assay GST-MAGI-3-PDZ2
      binding peptide
<220> FEATURE:
<221> NAME/KEY: MOD_RES
<222> LOCATION: (1)
<223> OTHER INFORMATION: Xaa = Pro modified by OregonGreen

<400> SEQUENCE: 3

Xaa Phe Asp Glu Asp Gln His Thr Gln Ile Thr Thr Val
 1               5                  10

<210> SEQ ID NO 4
<211> LENGTH: 15
<212> TYPE: PRT
<213> ORGANISM: Artificial Sequence
<220> FEATURE:
<223> OTHER INFORMATION: Description of Artificial Sequence:peptide for
      producing anti-phospho-Ser473 antibodies
<220> FEATURE:
<221> NAME/KEY: MOD_RES
<222> LOCATION: (9)
<223> OTHER INFORMATION: Xaa = phosphoserine

<400> SEQUENCE: 4

Cys Arg Pro His Phe Pro Gln Phe Xaa Tyr Ser Ala Ser Gly Thr
 1               5                  10                  15

<210> SEQ ID NO 5
<211> LENGTH: 11

```
<212> TYPE: PRT
<213> ORGANISM: Artificial Sequence
<220> FEATURE:
<223> OTHER INFORMATION: Description of Artificial Sequence:synthetic
      substrate peptide for kinase activity assay

<400> SEQUENCE: 5

Gly Arg Pro Arg Thr Ser Ser Phe Ala Glu Gly
 1               5                  10
```

US 7,141,600 B2

SMALL MOLECULE INHIBITION OF A PDZ-DOMAIN INTERACTION

CROSS-REFERENCES TO RELATED APPLICATIONS

This application claims the priority of U.S. provisional application 60/463,198 filed Apr. 15, 2003, the entire contents of which are hereby incorporated herein.

STATEMENT AS TO RIGHTS TO INVENTIONS MADE UNDER FEDERALLY SPONSORED RESEARCH OR DEVELOPMENT

This work was supported in part by National Institutes of Health grant no. GM31497. The government of the United States of America may have certain rights in this invention.

BACKGROUND AND FIELD OF THE INVENTION

This invention relates to the inhibition of interactions of PDZ domains of a protein or proteins with other proteins, and more particularly to novel compounds that have been found to be effective in inhibiting PDZ domains. In a very specific aspect, this invention relates to the inhibition of a PDZ domain of proteins that regulate the function of the oncogenic protein PTEN, or of the PDZ domain of the Dishevelled protein (Dvl), and compounds that have been found to possess such inhibiting capability. Compounds of the invention have been shown to produce apoptosis in cancer cells overexpressing Dvl.

PDZ domains are regions of signaling proteins that function to modulate protein-protein interactions such as protein-protein recognition. PDZ domains were named for three proteins in which this domain was initially discovered: PSD-95 (a 95 kDa protein involved in the signaling at the post-synaptic density), DLG [*Drosophila* lethal (1) discs large-1], and ZO-1 (the zonula occludens-1 protein involved in maintenance of epithelial polarity). These proteins play important roles in neuronal synaptic transmission, tumor suppression, and cell junction formation, respectively. They are understood as functioning in vivo by organizing multi-protein complexes that function in signaling, e.g. communication between cells. For example, PDZ-organized signaling complexes are known to function in communication involving neurons or epithelial cells, e.g., by coupling activated receptors to downstream second messenger systems, and in transporting and targeting proteins to sites of cellular signaling. They are involved in the functioning of important cell signal mediators including ion channels, transmembrane receptors, and regulatory enzymes. PDZ-containing proteins are believed to be involved in disorders associated with defective cell signaling, including ischemic nerve damage and tumorigenesis.

Structurally, PDZ domains are 80–90 amino acid modular protein interaction domains that comprise six beta-strands (betaA to betaF) and two alpha-helices, A and B, compactly arranged in a globular structure. Peptide binding of the ligand takes place in an elongated surface groove as an anti-parallel beta-strand interacts with the betaB strand and the B helix. The structure of PDZ domains allows binding to a free carboxylate group at the end of a peptide through a carboxylate-binding loop between the betaA and betaB strands.

Among proteins with PDZ domains are the MAGIs (membrane associated guanylate kinase proteins with inverse orientation). Proteins in this class participate in the assembly of multiprotein complexes on the inner surface of the plasma membrane at regions of cell-cell contact. The MAGIs are a small family of adaptors, widely expressed in the human body, that have six PDZ domains. MAGI-3 binds to the tumor suppressor PTEN, a lipid/protein phosphatase, using its second PDZ domain (MAGI3-PDZ2). The interaction of MAGI-3 and PTEN decreases phosphotidylinositol 3-kinase and Akt/PKB signaling whereas release of PTEN from MAGI-3 increases Akt/PKB signaling. Normally, Akt/PKB signaling ensures cell survival during response to cellular insults by suppressing apoptosis. However, PTEN mutants that cause constitutive Akt/PKB signaling have been associated with human cancers. Chemical disruption of this interaction would be a unique way to investigate the role Akt/PKB signaling in transformation and cancer, and could affect the development of cancerous growths.

Also among proteins that have been found to possess a PDZ domain is the Dishevelled protein (Dvl). Its interactions with the Wnt and Frizzled proteins have been indicated as being involved in one or more types of cancers.

Small-molecule inhibitors of interactions of proteins having PDZ domains with other proteins would be desirable.

BRIEF SUMMARY OF THE INVENTION

This invention relates to novel compounds that have been found effective in inhibiting PDZ domain interactions, and particularly interactions of PDZ domains in MAGIs with the oncogenic (tumor suppressor) protein PTEN, and of a PDZ domain in the Dishevelled protein with Frizzled proteins, and to the inhibition of PDZ domain activity by the use of these compounds.

The novel compounds have the general formula

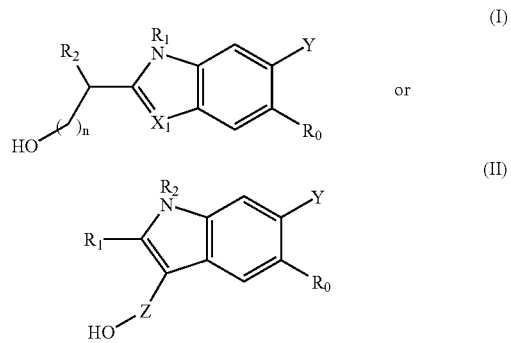

in which:

$R_0$ is selected from the group consisting of $C_1$–$C_3$ alkyl, cyclopropyl, halo, $OR_5$ and $S(O)_m R_5$ in which m is 0, 1 or 2;

$R_1$ and $R_2$ are independently selected from the group consisting of $C_2$–$C_8$ alkenyl, phenylcyclopropyl, phenylpropenyl, $R_6$—$X_2$—$C(R_8)(R_8)$—$R_7$—; and $R_6$—$X_2$—$N(R_8)$—$R_7$—;

$R_3$ and $R_4$ are independently hydrogen, methyl or ethyl;

$R_5$ is methyl or ethyl;

$R_6$ is selected from the group consisting of hydrogen, $C_1$–$C_{10}$ alkyl, aryl, W, Y, $NH_2$, $NHCONR_3R_4$, $NHCOOR_3$ and $NHSO_2R_9$;

$R_7$ is selected from the group consisting of a direct bond, an alkyl group having from 1 to 10 carbon atoms, aryl, —(NH)$_p$(CH$_2$CH$_2$O)$_q$(NH)$_p$— in which p is 0 or 1 and q is an integer from 1 to 4, and W;

R$_8$ is selected from the group consisting of H, Y, OH, —NHCONR$_3$R$_4$; —NHCOOR$_3$; —NHSO$_2$R$_9$, —(CH$_2$)$_r$CO$_2$R$_3$, and (CH$_2$)$_r$CO$_2$NR$_3$R$_4$ in which r is an integer from 1 to 3;

R$_9$ is aryl or C$_1$–C$_6$ alkyl;

X$_1$ is —CH—, —C-hal, —C(CH$_3$) or —C(C$_2$H$_5$), in which hal stands for a halogen atom (preferably chloro, fluoro or bromo);

X$_2$ is selected from the group consisting of a direct bond, —NH—, —N(CH$_3$)—, —NCONR$_3$R$_4$—, —NCOOR$_3$—, and NSO$_2$R$_9$;

W is a saturated carbocyclic or heterocyclic group;

Y is selected from the group consisting of COOH, COOR$_3$, CONR$_3$R$_4$, CONHSO$_2$R$_5$, hydroxymethyl, —CH$_2$COOH, CH$_2$CONR$_3$R$_4$; and 5-tetrazolyl; and Z is —CH$_2$—, —CH(CH$_3$)—, C(CH$_3$)$_2$— or —CO—;

and hydrates and salts thereof, and labeled derivatives thereof.

This invention also includes processes and intermediates for the preparation of these compounds. This invention also includes libraries of such compounds and methods for preparing such libraries. The invention also includes labeled versions of the compounds and chemical probes prepared by linking the novel compounds to various labeling moieties.

In another aspect, this invention includes methods for inhibiting the interaction of a PDZ domain of a protein with other proteins, more particularly the interaction of a MAGI protein or of the Dishevelled protein (Dvl) with other proteins, by contacting the protein that contains the PDZ domain, or the PDZ domain, with an inhibitory effective amount of a compound as defined herein. In yet another aspect this invention relates to methods of studying protein interactions and/or PDZ domain functioning that involves contacting the protein or the domain with a compound or compounds as described herein. The invention also includes arrays of such compounds for studying protein interactions or for screening proteins for PDZ domain activity.

In a more specific aspect of this, the invention comprises inhibiting interactions of PDZ domains in MAGIs with the oncogenic (tumor suppressor) protein PTEN or of inhibiting interactions between the PDZ domain in the Dishevelled protein and other proteins, for example the Frizzled (Fz) protein, by contacting the MAGI protein, the Dishevelled protein, or a PDZ domain of such protein with an effective inhibitory amount of a compound as described herein.

In another embodiment this invention also provides therapeutic methods of treating cancer comprising contacting the cancer or cancerous cells with an effective PDZ domain-inhibiting amount of a compound of the invention. In these embodiments, the cancer cell typically is in a patient and the step of contacting is carried out by administering a therapeutic agent, namely one or more compounds of the invention, or a composition containing the same, to the patient. The method may further comprise administering to the patient a second therapeutic agent, such as a chemotherapeutic agent or radiation therapy. The cancer cell may be a breast cancer cell, colorectal cancer cell, a lung cancer cell, a sarcoma cell, or a mesothelioma cell, a prostate cancer cell, a pancreatic cancer cell, a cervical cancer cell, an ovary cancer cell, a gastric cancer cell, an esophageal cancer cell, a head and neck cancer cell, a hepatocellular carcinoma cell, a melanoma cell, a glioma cell, a squamous cancer cell, or a glioblastoma cell.

U.S. patent application Ser. No. 10/678,639 filed Oct. 3, 2003, titled "Methods for Treating Cancer by Inhibiting WNT Signaling", of He et al., is hereby incorporated herein in its entirety. That application discloses inhibiting the growth of cancer cells that overexpress a Wnt protein by contacting the cell with an agent that inhibits binding of the Wnt protein to a Frizzled receptor. PCT application WO 02/088081 discloses that overexpression of Wnt appears connected to the occurrence of head and neck squamous cancer. Wong et al, *J. Mol. Cell* 12.1251 (November, 2003) disclosed that binding of the Dlv protein to Fz occurs at the PDZ domain of Frz. Inhibition of the PDZ-domain/Dlv interaction can thus inhibit Wnt signaling and consequently inhibit the growth of cancer cells The term "Frizzled protein" (Fz or Fzd) refers to a family of mammalian proteins related to the *Drosophila* frizzled genes, which play a role in the development of tissue polarity. The Frizzled family comprises at least 10 mammalian genes. Exemplary human Frizzled receptors include Frizzled1, Frizzled2, Frizzled3, Frizzled4, Frizzled5, Frizzled6, Frizzled7, Frizzled8, Frizzled9 and Frizzled10. Frizzled protein receptors are involved in a dynamic model of transmembrane signal transduction analogous to G-protein-coupled receptors with amino-terminal ligand binding domains.

The term "Dishevelled" or "Dvl" refers to a member of a family of Dishevelled proteins, the full-length sequences of which typically possess three conserved domains, a DIX domain, present in the Wnt antagonizing protein Axin; a PDZ domain involved in protein-protein interactions, and a DEP domain found in proteins that regulate Rho GTPases. Dvl proteins include, for example, Dvl-1, Dvl-2, and Dvl-3. Nucleic acid and protein Dvl sequence are known from a variety of species, including mouse and human. Exemplary human Dvl-1, Dvl-2, and Dvl-3 protein sequences are available under reference sequences NP_004412, NP_004413, and NM_004414, respectively.

"Inhibitors of Wnt signaling" refers to compounds that, e.g., bind to Dishevelled proteins so as to interfere with Dishevelled/Frizzled interaction, and consequently partially or totally block Wnt signaling, as measured for example, in known assays for Wnt signaling (e.g., measurement of y catenin levels, or oncogene expression controlled by Tcf and Lef transcription factors).

A "cancer cell that overexpresses a Wnt protein" is a cancer cell in which expression of a particular Wnt protein is at least about 2 times, usually at least about 5 times the level of expression in a normal cell from the same tissue. Methods for determining the level of expression of a particular gene are well known in the art. Such methods include RT-PCR, use of antibodies against the gene products, and the like.

In still another aspect this invention involves screening proteins for PDZ domain activity by contacting the proteins with a compound or compounds of the invention.

Studying the functioning of proteins having a PDZ domain or screening proteins for PDZ domain activity may involve the use of a single compound of the invention, or a number, including a large number of compounds of the invention. The latter may be carried out with a number of tests using individual proteins, or with arrays or libraries of such compounds. The compounds may be in the above-shown form or preferably also include a labeling moiety. Additionally, the compounds may be conjugated or bonded to a solid support, for example a plate or a particulate material, and such combinations of solid support and compounds are another aspect of this invention.

By "inhibitors" is meant compounds that, e.g., bind to, partially or totally block stimulation, decrease, prevent, or delay activation, or inactivate, desensitize, or down-regulate signal transduction. Similarly, the term "inhibition" means a partial or total blocking, stimulation, decrease, prevention or delaying of activation, or inactivation, desensitizing or down-regulation of signal transduction. An "effective inhibitory amount" of a compound or composition is an amount that produces inhibition in a particular assay or in a patient.

DETAILED DESCRIPTION OF THE INVENTION

Figure 1:
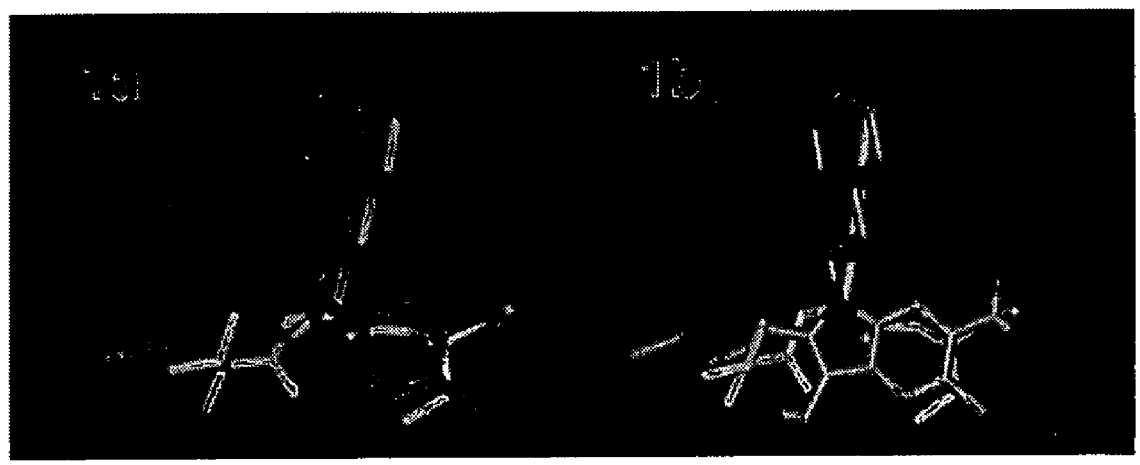
FIG. 1 depicts the overlay of the PTEN sequence TKV with compounds of this invention.

This invention relates to novel compounds that have been found effective in inhibiting PDZ domain interactions, particularly interactions of a PDZ domain in MAGIs with the oncogenic (tumor suppressor) protein PTEN and interactions of a PDZ domain in the Dishevelled protein with a Frizzled protein or receptor, and to the inhibition of PDZ domain activity by the use of these compounds.

The novel compounds have the general formulas:

(I)

or (II)

in which $R_0$ is selected from the group consisting of $C_1$–$C_3$ alkyl, cyclopropyl, halo, $OR_5$ and $S(O)_mR_5$ in which m is 0, 1 or 2;

$R_1$ and $R_2$ are independently selected from the group consisting of $C_2$–$C_8$ alkenyl, phenylcyclopropyl, phenylpropenyl,), $R_6$—$X_2$—$C(R_8)(R_8)$—$R_7$—; and $R_6$—$X_2$—N($R_8$)—$R_7$—;

$R_3$ and $R_4$ are independently hydrogen, methyl or ethyl;

$R_5$ is methyl or ethyl;

$R_6$ is selected from the group consisting of hydrogen, $C_1$–$C_{10}$ alkyl, aryl, W, Y, $NH_2$, $NHCONR_3R_4$, $NHCOOR_3$ and $NHSO_2R_9$;

$R_7$ is selected from the group consisting of a direct bond, an alkyl group having from 1 to 10 carbon atoms, aryl, —(NH)$_p$(CH$_2$CH$_2$O)$_q$(NH)$_p$— in which p is 0 or 1 and q is an integer from 1 to 4, and W;

$R_8$ is selected from the group consisting of H, Y, OH, —NHCONR$_3$R$_4$; —NHCOOR$_3$; —NHSO$_2$R$_9$, —(CH$_2$)$_r$CO$_2$R$_3$, and (CH$_2$)$_r$CO$_2$NR$_3$R$_4$ in which r is an integer from 1 to 3;

$R_9$ is aryl or $C_1$–$C_6$ alkyl;

$X_1$ is —CH—, —C-hal, —C(CH$_3$) or —C(C$_2$H$_5$), in which hal stands for a halogen atom (preferably chloro, fluoro or bromo);

$X_2$ is selected from the group consisting of a direct bond, —NH—, —N(CH$_3$)—, —NCONR$_3$R$_4$—, —NCOOR$_3$—, and NSO$_2$R$_9$;

W is a saturated carbocyclic or heterocyclic group;

Y is selected from the group consisting of COOH, COOR$_3$, CONR$_3$R$_4$, CONHSO$_2$R$_5$, hydroxymethyl, —CH$_2$COOH, CH$_2$CONR$_3$R$_4$; and 5-tetrazolyl; and Z is —CH$_2$—, —CH(CH$_3$)—, C(CH$_3$)$_2$— or —CO—;

and hydrates and salts thereof, and labeled derivatives thereof.

Some preferred embodiments for $R_1$ and $R_2$ include $C_3$–$C_8$ alkyl; $C_3$–$C_6$ cycloalkyl; $C_3$–$C_8$ alkenyl; —(CH$_2$)$_m$C$_6$H$_5$ where m is 0 or an integer from 1–3; —CH$_2$OC$_6$H$_5$, CH$_2$COC$_6$H$_5$, phenyl($C_2$–$C_4$ alkenyl), or analogous moieties having substituted phenyl groups; optionally substituted phenylcyclopropyl; —(CH$_2$)$_s$OH, —(CH$_2$)$_s$CONH$_2$ and —(CH$_2$)$_s$COOH where s is an integer from 1 to 3; phenyl; thienyl; and optionally substituted $C_3$–$C_6$ cycloalkyl-($C_1$–$C_3$ alkyl). Particularly preferred embodiments are phenethyl, hydroxyethyl, n-butyl and n-pentyl.

In one preferred embodiment, the compounds are of formula (I), $R_1$ is other than hydroxyethyl or a phenethyl group, and $R_2$ is not an alkyl group optionally substituted by hydroxy. In another preferred embodiment the compounds are of formula (II), $R_1$ is other than an alkyl group, $R_2$ is not a phenethyl group and Z is CO.

The term "alkyl" as used herein means a straight or branched chain, or non-aromatic cyclical, hydrocarbon radical, or combination thereof, that is fully saturated and has the number of carbon atoms designated (i.e. $C_1$–$C_{10}$ means one to ten carbon atoms). Examples of acyclic alkyl groups include, but are not limited to, groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like. Examples of cyclical alkyl groups include cyclopropyl, cyclobutyl, cyclopentyl, cyclohexyl, and the like. The term "lower alkyl" means a group of the type mentioned, having up to ten, preferably up to six, carbon atoms. For use in the invention, alkyl groups generally may be of any desirable size. Preferably they will contain up to 20, more preferably, up to 10, and most preferably up to 8, carbon atoms.

The term "alkenyl" as used herein means a straight or branched chain, or non-aromatic cyclical, hydrocarbon radical, or combination thereof, that contains one or more olefinic bonds and has the number of carbon atoms designated (i.e. $C_1$–$C_{10}$ means one to ten carbon atoms). Examples of acyclic alkenyl groups include, but are not limited to, groups such as vinyl, allyl, propenyl, butenyl, crotyl, butadienyl, and the like. Examples of cyclical alkyl groups include cyclopentenyl, cyclohexenyl, cyclohexadienyl, and the like. For use in the invention, alkenyl groups generally may be of any desirable size. Preferably they will contain up to 20, more preferably, up to 10, and most preferably up to 8, carbon atoms.

The alkyl and alkenyl groups used in this invention may be unsubstituted or may be mono- or polysubstituted, as indicated above.

Substituted alkyl, alkenyl, or cycloalkyl groups also include arylalkyl groups, namely alkyl (including cycloalkyl) groups substituted by one or more aryl groups; for instance, benzyl, phenethyl, triphenylmethyl, phenylpropenyl, cyclohexylmethyl, cyclopropylmethyl, and the like. They also may include cycloalkyl groups having an aryl group as a substituent such as phenylcyclopropyl. The aromatic ring or rings in the arylalkyl groups may be further substituted similarly to other aliphatic groups, e.g. chlorobenzyl, methylbenzyl, etc. Substituted alkyl groups also include alkyl groups substituted by one or more saturated or unsaturated heterocyclic groups, i.e. the substituted alkyl groups are pyridylmethyl, pyridylethyl, piperidinylmethyl, pyrrolidinylmethyl, morpholinylmethyl, quinolylmethyl, etc. Such groups may be substituted by one or more halogens, hydroxyl groups, lower alkyl groups, or lower alkoxy groups (including combinations of such groups).

As used herein, "aryl" refers to the typical substituted or unsubstituted non-aliphatic hydrocarbyl groups of this class, i.e., a polyunsaturated, typically aromatic, hydrocarbon substituent, which can be a single ring or multiple rings (up to three rings) which are fused together or linked covalently, such as phenyl, naphthyl, and the like. This class of moieties also includes fused-ring moieties such as indanyl, etc. Substituents for the aromatic moieties are similar to those for the aliphatic groups. "Aryl", as used herein, also includes analogous heterocyclic groups (sometimes termed "heteroaromatic" groups), namely polyunsaturated cyclical moieties containing carbon atoms in the ring and additionally one or more hetero atoms, which are typically oxygen, nitrogen, sulfur and or phosphorus, such as pyridinyl, pyrazinyl, pyrazolyl, thienyl, furyl, thiazolyl, imidazolyl, pyrrolyl, etc., and fused-ring moieties such as benzoxazolyl, benzthiazolyl, etc. These may be optionally substituted with one or more substituents such as halogen, hydroxy, amino, optionally substituted lower alkyl, optionally substituted lower alkoxy, $NCONR_3R_4$ and $NCOOR_3$, and other substituents included above within the definition of group $R_6$.

Aryl compounds also include fluorescent aromatic moieties such as

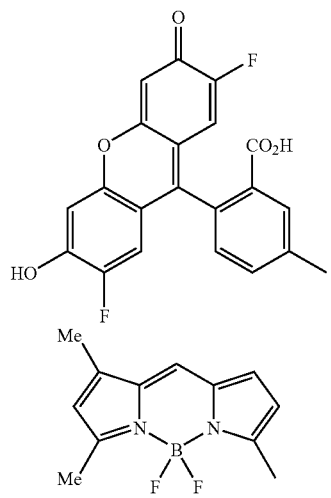

Carbocyclic or heterocyclic moieties for W generally have the formula

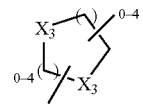

and are, for example:

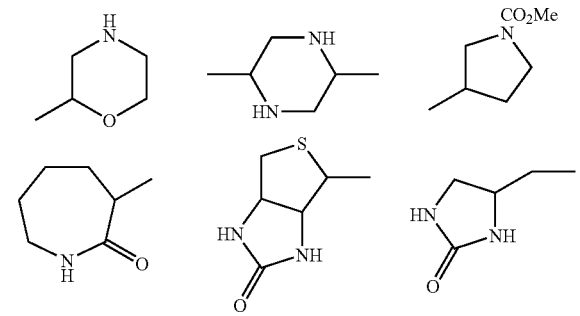

In general, compounds of Formula (I) may be synthesized from a starting nitrobenzene or aminobenzene

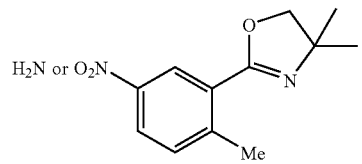

followed by iodination and closure to form an indole, and alkylation or the like to add groups $R_1$ and $R_2$ and replacement of the oxazolidine group by a group Y. An illustration of such a method is shown below.

The following Tables I and II show representative compounds of the invention, that can be made by the processes described herein

TABLE 1

(Compounds of Formula I)

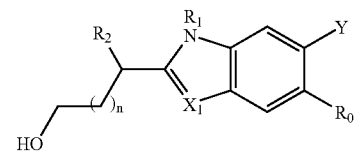

| Cmpd. No. | $R_0$ | $R_1$ | $R_2$ | Y | n |
|---|---|---|---|---|---|
| 1 | $CH_3$ | $C_2H_4C_6H_4$ | $n\text{-}C_4H_9$ | COOH | 0 |
| 2 | $CH_3$ | $CH_2CH_2OH$ | $n\text{-}C4H_9$ | COOH | 0 |
| 3 | $CH_3$ | $CH_2CH_2OH$ | $CHOH(CH_2)_3$—$CONH_2$ | COOH | 0 |
| 4 | $CH_3$ | $C_2H_4C_6H_5$ | $C_6H_5$ | COOH | 0 |
| 5 | $CH_3$ | $C_2H_4C_6H_5$ | $CHOH(CH_2)_3$—$CONH_2$ | COOH | 0 |

TABLE 2

Compounds of Formula (II)

| Cmpd. No. | $R_0$ | $R_1$ | $R_2$ | Y | Z |
|---|---|---|---|---|---|
| 6 | $CH_3$ | n-$C_5H_{11}$ | $C_2H_4C_6H_5$ | COOH (Na salt) | $CH_2$ $CH_2$ |
| 7 | $C_2H_5$ | n-$C_5H_{11}$ | $C_2H_4C_6H_5$ | COOH (Na salt) | $CH_2$ |

A 6×8 procedure that may be used to prepare compounds of the invention is shown below. The procedure shows preparation of the AcO— and —COOCH$_3$ analogs of these compounds, which are then converted to the compounds of the invention having —OH and —COOH groups, respectively.

patient or subject in an amount sufficient to elicit an effective therapeutic response in the patient. An amount adequate to accomplish this is defined as an "effective inhibitory amount," a "therapeutically effective dose" or a "therapeutically effective amount". The dose or amount will be determined by the efficacy of the particular active substance employed and the condition of the subject. The size of the dose also will be determined by the existence, nature, and extent of any adverse effects that accompany the administration of a particular compound in a particular subject. Typically, the patient or subject is human. However, the patient or subject may be a non-human mammal (e.g., a primate, a mouse, a pig, a cow, a cat, a goat, a rabbit, a rat, a guinea pig, a hamster, a horse, a sheep, a dog, a cat and the like), and may be male or female.

Toxicity and therapeutic efficacy of the compounds can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic

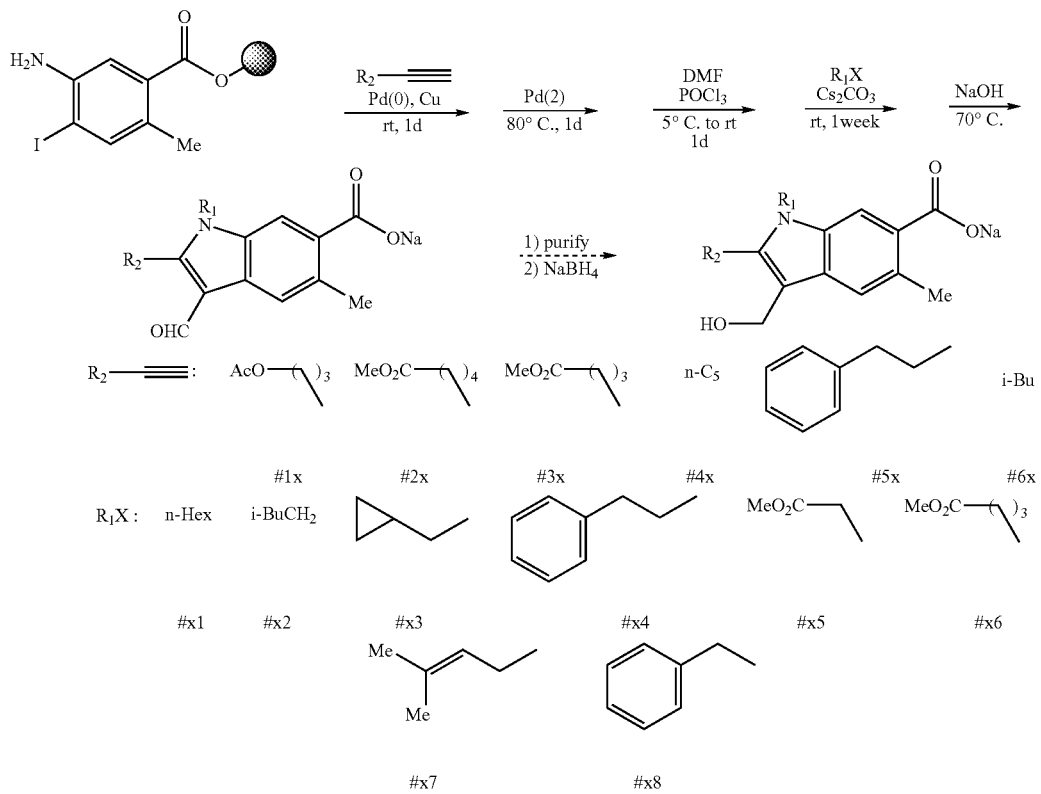

Formulation and Administration

Compounds of the invention that inhibit interactions between the PDZ domain of a protein and other proteins can be administered to a patient or subject at doses effective to provide the desired inhibition, or at therapeutically effective doses to prevent, treat, or control conditions, for example to act as neuroprotecting drugs and anti-tumor agents. Compositions containing the substances are administered to a indices are preferred. While compounds that exhibit toxic side effects can be used, care should be taken to design a delivery system that targets such compounds to the site of affected tissue to minimize potential damage to normal cells and thereby reduce side effects.

The data obtained from cell culture assays and animal studies can be used to formulate a dosage range for use in humans. The dosage of such compounds lies preferably within a range of circulating concentrations that include the $ED_{50}$ with little or no toxicity. The dosage can vary within this range depending upon the dosage form employed and the route of administration. For any compound used in the methods of the invention, the therapeutically effective dose can be estimated initially from cell culture assays. A dose can be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC).

Pharmaceutical compositions for use in the present invention can be formulated by standard techniques using one or more physiologically acceptable carriers or excipients. The compounds and their physiologically acceptable salts and solvates can be formulated for administration by any suitable route, including via inhalation, topically, sublingually, intranasally, orally, parenterally (e.g., intravenously, intraperitoneally, intramuscularly, subcutaneously, intravesically or intrathecally), or mucosally (including intranasally, orally and rectally).

For oral or sublingual administration, pharmaceutical compositions of compositions of the invention can take the form of, for example, lozenges, tablets or capsules prepared by conventional means with pharmaceutically acceptable excipients, including binding agents, for example, pregelatinized cornstarch, polyvinylpyrrolidone, or hydroxypropyl methylcellulose; fillers, for example, lactose, microcrystalline cellulose, or calcium hydrogen phosphate; lubricants, for example, magnesium stearate, talc, or silica; disintegrants, for example, potato starch or sodium starch glycolate; or wetting agents, for example, sodium lauryl sulfate. Tablets can be coated by methods well known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active compound.

For administration by inhalation, the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds can be formulated for parenteral administration by injection, for example, by bolus injection or continuous infusion. Formulations for injection can be presented in unit dosage form, for example, in ampoules or in multi-dose containers, with an added preservative. The compositions can take such forms as suspensions, solutions, or emulsions in oily or aqueous vehicles, and can contain formulatory agents, for example, suspending, stabilizing, and/or dispersing agents. Alternatively, the active ingredient can be in powder form for constitution with a suitable vehicle, for example, sterile pyrogen-free water, before use.

The compositions of the invention may also be formulated in rectal compositions such as suppositories or retention enemas, e.g., containing conventional suppository bases such as cocoa butter or other glycerides.

The compositions of the invention may also be formulated for transdermal administration. For transdermal administration, the active compounds are formulated into ointments, salves, gels, or creams as generally known in the art. Pharmaceutical compositions adapted for transdermal administration can be provided as discrete patches intended to remain in intimate contact with the epidermis for a prolonged period of time. If the compositions of the invention are to be administered topically, the compositions can be formulated in the form of, e.g., an ointment, cream, transdermal patch, lotion, gel, spray, aerosol, solution, emulsion, or other form well-known to one of skill in the art. For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as Freon), or in a squeeze bottle. Moisturizers or humectants can also be added to pharmaceutical compositions and dosage forms if desired. Examples of such additional ingredients are well-known in the art. Compositions may also be included in a device for transdermal delivery such as a skin patch or a more complex device.

The compounds also may be formulated as a depot preparation. Such long-acting formulations can be administered by implantation (for example, subcutaneously or intramuscularly) or by intramuscular injection. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

The compositions may also be in the form of controlled release or sustained release compositions as known in the art, for instance, in matrices of biodegradable or non-biodegradable injectable polymeric microspheres or microcapsules, in liposomes, in emulsions, and the like.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

Depending on their chemical and physical nature, compounds of the invention may be included in the compositions and administered to the patient per se, or in another form such as a salt, solvate, complex, chelate or other derivative as appropriate or as needed for good formulation or administration of the substance. Likewise, a prodrug of the substance may be included in the compositions, that is, a substance that releases the active substance either on preparation of the composition or on administration of the composition to the patient or subject.

As mentioned above, this invention also provides therapeutic methods of treating cancer comprising administering one or more compounds of the invention, or a composition containing the same, to the patient. The method may further comprise administering to the patient a second therapeutic agent, such as a chemotherapeutic agent or radiation therapy. The cancer being treated may be a breast cancer, a colorectal cancer, a lung cancer, a sarcoma, a mesothelioma, a prostate cancer, a pancreatic cancer, a cervical cancer, an ovary cancer, a gastric cancer, an esophageal cancer, a head and neck cancer, a hepatocellular carcinoma, a melanoma, a glioma, a squamous cancer, or a glioblastoma.

In carrying out the invention, a single inhibitory compound, or a combination of compounds according to this invention may be administered to a patient. The effective compounds may be administered alone or in combination with (or in time proximity to) other therapeutic agents administered for similar or other therapeutic purposes, for example administration of a compound according to this invention together with an adjuvant or other anti-inflammatory agent. Similarly, compositions containing one or more of the compounds of this invention may also contain other pharmaceutical or therapeutic agents.

The present invention also includes arrays for testing substances for interaction with or inhibition of PDZ domains. Typically such arrays will be used for testing combinatorial or other libraries. The arrays will comprise standard equipment such as a plate, which will contain compounds arranged on the surface of the plate, for example in wells or bound to certain locations on the surface. A plate or array may contain compounds of a single type or it may contain different compounds, located in prearranged fashion.

In one aspect therefore the invention provides in vitro, ex vivo, and in vivo assays for inhibitors of proteins having PDZ domains or for studying inhibition of the activity of a given PDZ domain or a protein containing one. In particular, the assays can be used to test for compounds that possess this activity for testing for binding to, or inhibition of the activity of, PDZ domains. Typically in such assays, the compound or compounds to be tested are contacted with the protein having a PDZ domain and suitable tests are carried out to ascertain whether the normal activity of that domain has been inhibited. For example, the results of the assay may be compared to a control assay that comprises the protein alone, without the test compound(s), using any known activity of the protein as the comparison standard.

Alternatively screening of a compound for inhibition of PDZ domain activity of a protein may comprise contacting such a protein or a cell containing or expressing it with a compound of the invention and detecting specific binding of the compound to the domain. The detecting may be carried out via a method such as capillary electrophoresis, Western blot, mass spectroscopy, ELISA, immunochromatography, or immunohistochemistry.

Binding of test compounds to PDZ domains of proteins can be performed in solution, in a bilayer membrane, attached to a solid phase, in a lipid monolayer, or in vesicles. Binding of test compounds can be tested by measuring or observing changes in activity or by, e.g., changes in spectroscopic characteristics or in chromatographic or solubility properties. Binding of test compounds can also be ascertained in competitive binding assays, for example, by ascertaining whether unlabeled test compounds prevent the interaction between the protein and a biotinylated or fluorescent derivative of a reference compound.

The assays that form an aspect of this invention may be designed to screen large chemical libraries for inhibition of one or more of the proteins using automated assay steps, which are typically run in parallel (e.g., in microtiter formats on microtiter plates in robotic assays). In one preferred embodiment, high throughput screening methods are used that involve providing a combinatorial chemical or other library containing a large number of potential inhibitory compounds. Such libraries are then screened in one or more assays, as described herein, to identify those library members (either particular chemical species or subclasses) that display the desired activity. When screening for modulators, a positive assay result need not indicate that particular test agent is a good pharmaceutical. Rather, a positive test result can simply indicate that the test agent can be used to inhibit activity of a PDZ domain of a protein. The compounds thus identified may serve as conventional "lead compounds" for PDZ domain inhibitor discovery or may themselves be used as potential or actual therapeutics.

Thus, another aspect of this invention lies in libraries, such as combinatorial libraries, of compounds that are produced for testing based on activity, i.e., inhibition of a PDZ domain as described herein, within the general definitions of compounds herein, such as formulas (I)-(II). A combinatorial chemical library is a collection of such chemical compounds generated by either chemical synthesis or biological synthesis, by combining a number of chemical "building blocks" such as reagents. For example, a linear combinatorial chemical library is formed by combining a set of chemical building blocks in every possible way for a given compound type.

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.).

Chemical libraries containing a multiplicity of compounds of Formulas (I) or (II), respectively, are an aspect of this invention and may be synthesized by conducting parallel syntheses as described above for individual compounds.

The compounds used in screening or testing for inhibition of PDZ domain functioning are typically supported on a solid inert support, which may be particulate or non-particulate. Typically the immobilization is achieved by covalently or otherwise bonding the compounds to the solid support material. The bond may be made via a moiety that is part of the chemical composition of the support or that is attached to it, for example to provide an activated surface (for instance, in the case of glass). Numerous types of solid supports suitable for immobilizing compounds are known in the art. These include nylon, nitrocellulose, activated agarose, diazotized cellulose, latex particles, plastic, polystyrene, glass and polymer coated surfaces. These solid supports are used in many formats such as membranes, microtiter plates, beads, probes, dipsticks etc. A wide variety of chemical procedures are known to covalently link various compounds directly or through a linker to these solid supports.

Typically the use of any solid support requires the presence of a nucleophilic group to react with a compound that must contain a "reactive group" capable of reacting with the nucleophilic group. Alternatively, a "reactive group" is present or is introduced into the solid support to react with a nucleophile present in or attached to the oligonucleotide. Suitable nucleophilic groups or moieties include hydroxyl, sulfhydryl, amino and activated carboxyl groups, while the groups capable of reacting with these and other nucleophiles (reactive groups) include dichlorotriazinyl, alkylepoxy, maleimido, bromoacetyl groups and others. Chemical procedures to introduce the nucleophilic or the reactive groups onto solid support are known in the art, and include procedures to activate nylon (U.S. Pat. No. 5,514,785), glass (Rodgers et al., Anal. Biochem., 23–30 (1999)), agarose (Highsmith et al., J., Biotechniques 12: 418–23 (1992) and polystyrene (Gosh et al., Nuc. Acid Res., 15: 5353–5372 (1987)). Dependent on the presence of either a reactive or nucleophilic groups on the solid support and in the test compound, coupling can either be performed directly or with bifunctional reagents. Bifunctional and coupling reagents are well known in the art and many are available from commercial sources.

Typically, glass surfaces are activated by the introduction of amino-, sulfhydryl-, carboxyl- or epoxyl-groups to the glass using the appropriate siloxane reagent. Specifically, immobilization of oligonucleotide arrays on glass supports has been described: by Guo et al., Nuc. Acid Res., 22: 5456–5465 (1994) using 1,4-phenylene diisothiocyanate; by Joos et al., Anal. Biochem., 247: 96–101 (1997) using succinic anhydride and carbodiimide coupling; and by Beatti, et al., Mol. Biotech., 4: 213–225 (1995) using 3-glycidoxypropyltrimethoxysilane.

The following are examples of the preparation of compounds according to this invention.

Synthesis of PDZ domain inhibitors [1-(2-hydroxyethyl)-2-(1-Hydroxypentyl)-5-methyl]indole-6-carboxylic acid (2) and [2-(1-Hydroxypentyl)-5-methyl-1-(2-phenylethyl)]indole-6-carboxylic acid (3) [Formula (I) Table 1, compounds 2 and 1, respectively]

The general scheme for these syntheses was:

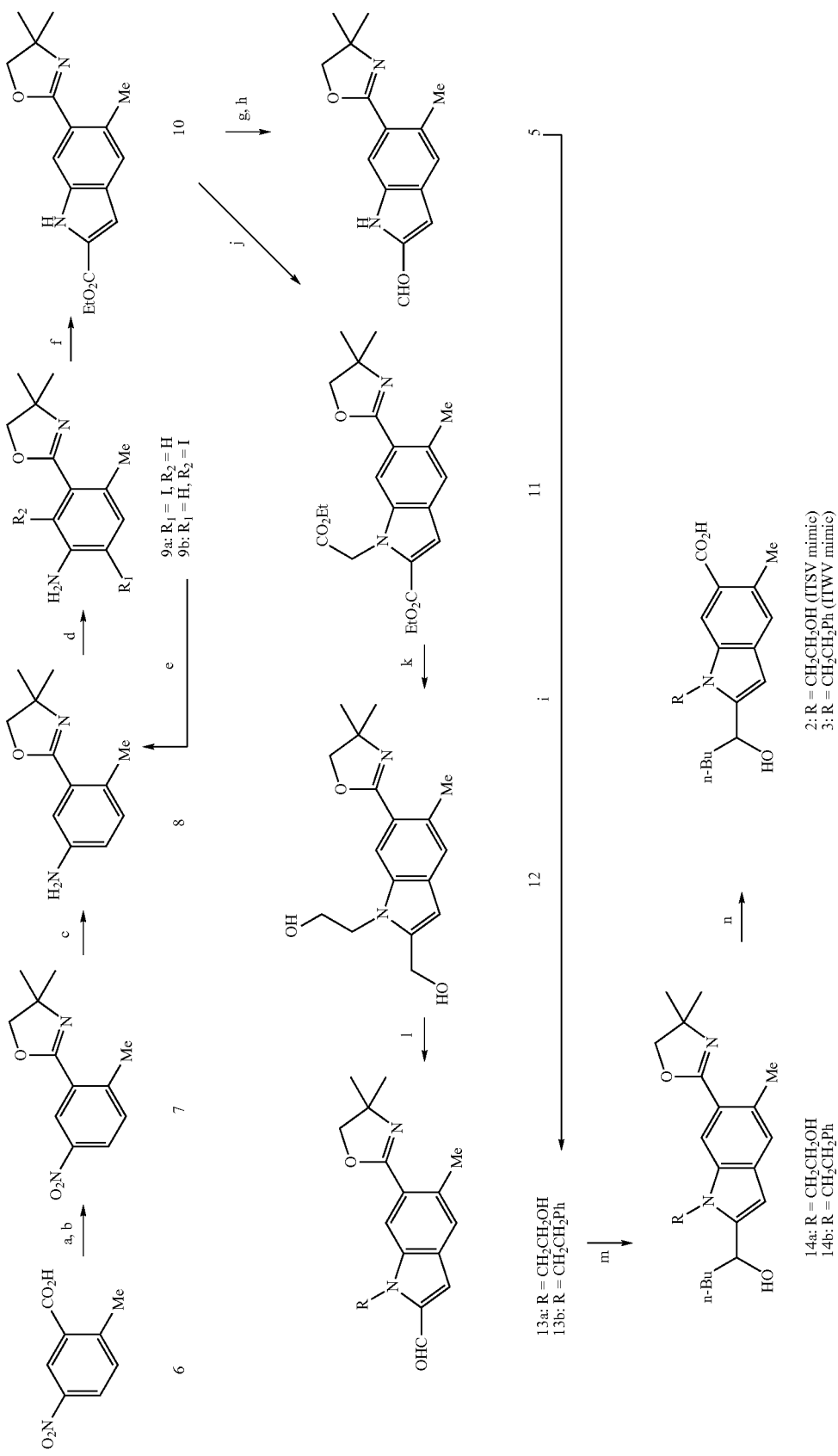

a) HOCH$_2$C(CH$_3$)$_2$NH$_2$ (3 eq), HBTU (1.2 eq), DIPEA (2 eq), DMF, 40° C., 14 hr. b) SOCl$_2$ (5 eq), CH$_2$Cl$_2$, rt, 0.5 hr. c) Fe (7.8 eq), NH$_4$Cl (aq), EtOH, reflux, 3 hr, 92% over 3 steps. d) ICl (1.6 eq), CaCO$_3$ (30 eq), MeOH, H$_2$O, rt, 1 hr. 9a: 36%, 9b: 47%. e) H$_2$, Pd—C, MeOH, Et$_3$N, rt, 1 hr, quant. f) Ethyl pyruvate (5 eq), Pd(OAC)$_2$ (0.2 eq), DABCO (5 eq), DMF, 105° C., 50 min, 44%. g) LiAlH$_4$ (10 mol), THF, reflux, 2.5 hr, 75%. h) MnO$_2$ (1.8 eq), CH$_2$Cl$_2$, rt, 12 hr, 76%. i) BrCH$_2$CH$_2$Ph (5 eq), K$_2$CO$_3$ (10 eq), DMF, 40° C., 22 hr, 93%. j) BrCH$_2$CO$_2$Et (1.05 eq), NaH (1.1 eq), DMF, 0° C., 10 min, 74%. k) LiAlH$_4$ (20 eq), THF, reflux, 0.5 hr, 58%. l) MnO$_2$ (19 eq), CH$_2$Cl$_2$, rt, 12 hr, 84%. m) n-BuMgBr (5 eq), 0° C., 0.5 hr, 14a: 72%, 14b: 87%. n) i. MeI (large excess), K$_2$CO$_3$ (3 eq), acetone, rt, 2.5 d; ii. NaOH, H$_2$O, MeOH, reflux, 7 hr, 2 steps overall 4a: 65%, 4b: 89%. o) MeI (large excess), K$_2$CO$_3$ (large excess), acetone, rt, 1.5 h, 69%. p) H$_2$, 10% Pd—C, HCl (20 eq), MeOH, rt, 1 hr, 25%.

Scheme for Synthesis of PDZ domain inhibitor Sodium[3-hydroxymethyl-2-(1-pentyl)-1-(2-phenylethyl)-5-methyl]indole-6-carboxylate (4) [Formula (II); Table 2, compound 6]

The general scheme for the synthesis of this compound was:

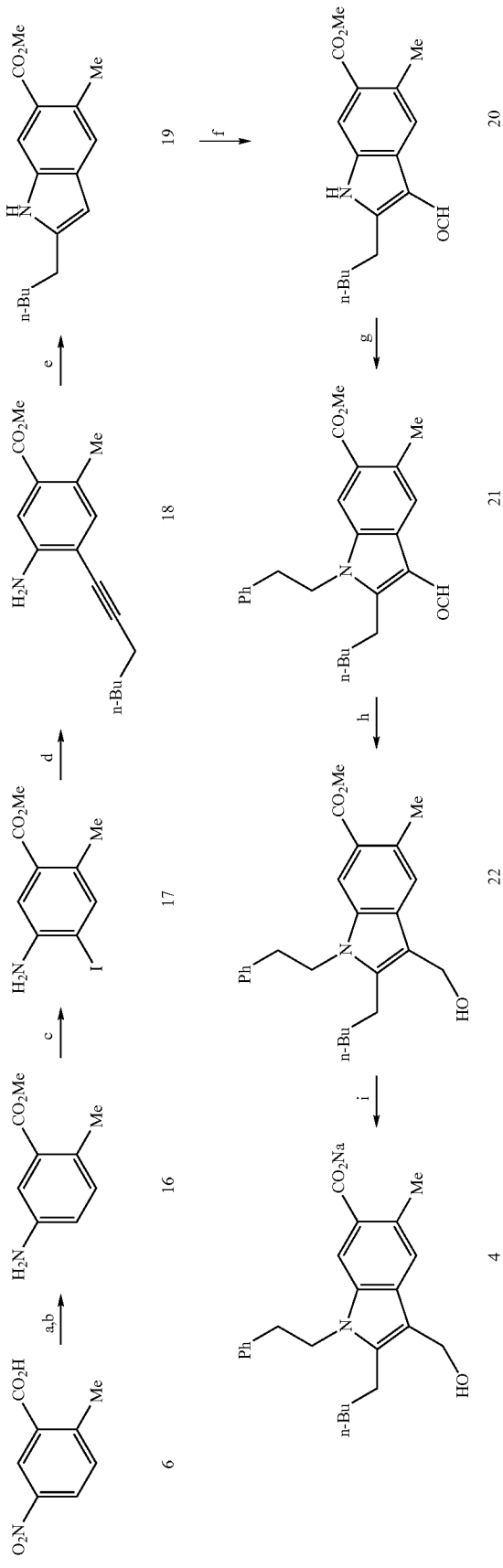

a) MeI (2 eq.), $K_2CO_3$ (3 eq.), DMF, 40° C., 1 hr. b) $H_2$, 10% Pd—C, MeOH, rt, 2 hr, 2 steps quant. c) ICl (1.6 eq), $CaCO_3$ (3 eq), MeOH, $H_2O$, rt, 1 hr, 34%. d) 1-heptyne (5 eq.), $PdCl_2$ $(PPh_3)_2$ (0.15 eq.), CuI (0.3 eq.), $Et_2NH$ (large excess), DMF, rt, 2 hr. e) $PdCl_2$ $(PhCN)_2$ (0.2 eq.), DMF, 80° C., 40 min, 2 steps overall 87%. f) $POCl_3$ (1.3 eq.), DMF, 5° C., quant. g) $BrCH_2CH_2Ph$ (10 eq), $Cs_2CO_3$ (5 eq), DMF, rt, 19 hr, 44%. h) $NaBH_4$ (excess), MeOH, 5° C. i) NaOH, $H_2O$, MeOH, 65° C., 12 hr.

2-[(3-Amino-6-methyl)phenyl]-4,4-dimethyloxazoline (8). A mixture of 2-methyl-5-nitrobenzoic acid (6, 1.0 g, 4.8 mmol), 2-amino-2-methylpropanol (0.64 g, 7.2 mmol), HBTU (2.2 g, 5.8 mmol), N,N-diisopropylethylamine (1.7 mL, 9.7 mmol), and DMF (5 mL) was stirred at 40° C. for 2 hours. Additional 2-amino-2-methylpropanol (0.64 g, 7.2 mmol) was added and stirred at 40° C. for 12 hours. The reaction mixture was diluted with ethyl acetate (50 mL) and washed with water twice (50 mL each) followed by brine (50 mL), dried ($Na_2SO_4$), and evaporated to give amide as pale-brown solid: $^1H$ NMR ($CDCl_3$, 400 MHz) δ 8.19 (d, J=2.4 Hz, 1H), 8.17 (dd, J=2.4 Hz and 8.4 Hz, 1H), 7.39 (d, J=8.4 Hz, 1H), 5.96 (broad s, 1H), 3.98 (broad s, 1H), 3.73 (s, 2H), 2.54 (s, 3H), 1.44 (s, 6H): 13C NMR ($CDCl_3$, 100 MHz) δ 168.74, 145.98, 144.12, 137.94, 132.22, 124.69, 121.85, 70.42, 57.21, 24.65, 20.12: EIHRMS m/z found: 221.0928 ($M—CH_2OH$, calcd. for $C_{11}H_{13}N_2O_3$: 221.0926). The crude amide was treated with thionyl chloride dichloromethane solution (2 M, 12 mL) at room temperature for 0.5 hours. The reaction mixture was poured into ice (50 g), added 10% aqueous sodium hydroxide solution (30 mL), extracted with ethyl acetate twice (40 mL each). The organic layer was washed with water twice (50 mL each) followed by brine (50 mL), dried (Na2SO4), and evaporated to give oxazoline 7 as a pale-brown oil. 7: 1H NMR ($CDCl_3$, 400 MHz) δ 8.60 (d, J=2.4 Hz, 1H), 8.13 (dd, J=2.4 Hz and 8.4 Hz, 1H), 7.37 (d, J=8.4 Hz, 1H), 4.08 (s, 2H), 2.66 (s, 3H), 1.38 (s, 6H): $^{13}C$ NMR ($CDCl_3$, 100 MHz) δ 160.45, 146.73, 146.10, 132.29, 129.06, 125.20, 124.89, 78.97, 68.76, 28.64, 22.14: EIHRMS m/z found: 234.1004 (calcd for $C_{12}H_{14}N_2O_3$: 234.1004). A mixture of crude 7, ethanol (5 mL), saturated aqueous ammonium chloride solution (0.5 mL), and iron powder (1.3 g) was heated under reflux for 1 hour. Additional iron powder (0.8 g) was added to the reaction mixture and continued the heating for 2 hours. The reaction mixture was filtered and was diluted with ethyl acetate (50 mL) and washed with water twice (50 mL each) followed by brine (50 mL), dried ($Na_2SO_4$), and evaporated to give 8 (896 mg, 92%). 8: reddish oil, $^1H$ NMR ($CDCl_3$, 400 MHz) δ 7.11 (d, J=2.4 Hz, 1H), 6.99 (d, J=7.6 Hz, 1H), 6.67 (dd, J=2.4 Hz and 8.0 Hz), 4.05 (s, 2H), 3.6 (broad s, 2H), 2.42 (s, 3H), 1.37 (s, 6H): $^{13}C$ NMR ($CDCl_3$, 100 MHz) δ 163.30, 144.06, 132.05, 128.22, 128.20, 117.66, 116.45, 78.81, 67.68, 28.58, 20.48: EIHRMS m/z found: 204.1270 (calcd for $C_{12}H_{16}N_2O$: 204.1263).

2-[(3-Amino-4-iodo-6-methyl)phenyl]-4,4-dimethyloxazoline (9a) and 2-[(3-Amino-2-iodo-6-methyl)phenyl]-4,4-dimethyloxazoline (9b). Iodine monochloride dichloromethane solution (1 M, 4.1 mL) was added to a mixture of 8 (522 mg, 2.56 mmol), methanol (5 mL), water (0.5 mL), and calcium carbonate (0.78 g, 7.8 mmol) at 0° C. and stirred at room temperature for 1 hour. The reaction mixture was stirred with a solution of sodium sulfite (0.53 g) in water (2 mL) at room temperature for 1 hour, filtered and concentrated under reduced pressure. The concentrated solution was diluted with ethyl acetate (30 mL) and washed with water twice (30 mL each) followed by brine (30 mL), dried ($Na_2SO_4$), and evaporated. The residue was purified with flash chromatography (silica gel, 2:1 n-hexane/ethyl acetate) to give 9a (304 mg, 36%) and 9b (394 mg, 47%). 9a: pale-brown solid, $^1H$ NMR ($CDCl_3$, 400 MHz) δ 7.51 (s, 1H), 7.16 (s, 1H), 4.05 (s, 2H), 3.99 (broad s, 2H), 2.39 (s, 3H), 1.36 (s, 6H): $^{13}C$ NMR ($CDCl_3$, 100 MHz) δ 162.56, 144.73, 141.19, 129.68, 128.69, 115.71, 87.28, 78.88, 67.87, 28.60, 20.17: EIHRMS m/z found: 330.0220 (calcd for $C_{12}H_{15}IN_2O$: 330.0229). 9b: pale-brown solid, $^1H$ NMR ($CDCl_3$, 400 MHz) δ 6.96 (d, J=8.4 Hz), 6.69 (d, J=8.0 Hz), 4.15 (s, 2H), 4.06 (broad s, 2H), 2.27 (s, 3H), 1.45 (s, 6H).

Ethyl [6-(4,4-dimethyloxazolin-2-yl)-5-methyl]indole-2-carboxylate (10). A mixture of 9a (2.48 g, 7.51 mmol), ethyl pyruvate (4.2 mL, 38 mmol), DABCO (4.2 g, 38 mmol), palladium acetate (337 mg, 1.50 mmol) and DMF (22.5 mL) was stirred at 105° C. for 50 minutes. The reaction mixture was diluted with ethyl acetate (100 mL) and washed with water twice (100 mL each) followed by brine (100 mL), dried ($Na_2SO_4$), and evaporated. The residue was purified with flash chromatography (silica gel, 2:1 n-hexane/ethyl acetate) to give 10 (985 mg, 44%). 10: pale-brown solid, $^1H$ NMR ($CDCl_3$, 400 MHz) δ 8.85 (s, 1H), 7.86 (s, 1H), 7.50 (s, 1H), 7.12 (s, 1H), 4.41 (quartet, J=6.8 Hz, 2H), 4.10 (s, 2H), 2.62 (s, 3H), 1.41 (s, 6H), 1.41 (t, J=4.4 Hz): $^{13}C$ NMR ($CDCl_3$, 100 MHz) δ 163.53, 162.09, 135.01, 130.25, 129.47, 129.28, 125.50, 123.87, 114.01, 107.88, 78.84, 68.05, 61.34, 28.63, 21.82, 14.56: EIHRMS m/z found: 300.1473 (calcd for $C_{17}H_{20}N_2O_5$: 300.1474).

[6-(4,4-Dimethyloxazolin-2-yl)-5-methyl]indole-2-carboxaldehyde (5). To a suspension of lithium aluminum hydride (0.49 g, 12.7 mmol) in THF (1 mL), a solution of 10 (766 mg, 2.55 mmol) in THF (6 mL) was added at 0° C. and heated under reflux. After 2 hours, additional suspension of lithium aluminum hydride (0.49 g, 12.7 mmol) in THF (3 mL) was added at 0° C. and heated under reflux for 0.5 hours. The reaction mixture was worked up in a standard manner. The crude product was washed with 5% ethyl acetate in n-hexane and dried to give alcohol (491 mg, 75%): pale-brown solid, $^1H$ NMR ($CDCl_3$, 400 MHz) δ 8.28 (s, 1H), 7.68 (s, 1H), 7.36 (s, 1H), 6.29 (s, 1H), 4.78 (s, 2H), 4.11 (s, 2H), 2.57 (s, 3H), 1.42 (s, 6H): $^{13}C$ NMR ($CD_3OD$, 100 MHz) δ 167.74, 142.97, 135.89, 132.14, 128.85, 122.55, 121.80, 113.76, 100.07, 80.06, 68.06, 58.08, 28.50, 21.33: EIHRMS m/z found: 258.1362 (calcd for $C_{15}H_{18}N_2O_2$: 258.1368). Activated manganese oxide (188 mg) was added to a solution of the alcohol (315 mg, 1.22 mmol) in dichloromethane (30 mL), and stirred at room temperature for 12 hours. The reaction mixture was filtered and evaporated. The residue was washed with n-hexane and dried to give 5 (237 mg, 76%). 5: brown solid, $^1H$ NMR ($CDCl_3$, 400 MHz) δ 9.84 (s, 1H), 9.01 (s, 1H), 7.88 (s, 1H), 7.57 (s, 1H), 7.18 (s, 1H), 4.11 (s, 2H), 2.62 (s, 3H), 1.42 (s, 6H): $^{13}C$ NMR ($CDCl_3$, 100 MHz) □ 182.51, 163.27, 137.51, 136.33, 130.54, 128.89, 127.44, 124.51, 114.60, 114.07, 78.88, 68.17, 28.59, 21.72: EIHRMS m/z found: 256.1202 (calcd for $C_{15}H_{16}N_2O_2$: 256.1212).

[6-(4,4-Dimethyloxazolin-2-yl)-5-methyl-1-(2-phenylethyl)]indole-2-carboxaldehyde (13b). A mixture of 5 (80 mg, 0.31 mmol), 2-bromoethylbenzene (210 microL, 1.56 mmol), potassium carbonate (0.43 g, 3.1 mmol) and DMF (2 mL) was stirred at room temperature for 22 hours. The reaction mixture was diluted with ethyl acetate (20 mL) and washed with water twice (10 mL each) followed by brine (10 mL), dried ($Na_2SO_4$), and evaporated. The residue was purified with preparative thin-layer chromatography (silica gel, 3:1 n-hexane/ethyl acetate) to give 13 (105 mg, 93%). 13: pale-brown solid, $^1H$ NMR ($CDCl_3$, 400 MHz) δ9.82 (s, 1H), 7.70 (s, 1H), 7.55 (s, 1H), 7.25–7.15 (m, 6H), 4.77 (t, J=7.2 Hz, 2H), 4.12 (s, 2H), 3.04 (t, J=7.2 Hz, 2H), 2.62 (s, 3H), 1.43 (s, 6H): $^{13}$C NMR (CDCl$_3$, 100 MHz) □ 182.60, 163.06, 138.38, 138.27, 136.70, 130.46, 129.15, 128.60, 127.91, 127.20, 126.71, 124.61, 116.75, 112.49, 78.81, 68.29, 46.46, 37.09, 28.64, 21.74: EIHRMS m/z found: 360.1843 (calcd for C$_{23}$H$_{24}$N$_2$O$_2$: 360.1838).

1-[[6-(4,4-Dimethyloxazolin-2-yl)-5-methyl-1-(2-phenylethyl)]indol-2-yl]pentanol (14b). To a solution of 13 (54 mg, 0.15 mmol) in dry THF (0.5 mL), n-butylmagnesium bromide THF solution (1 M, 0.45 mL) was added at 0° C. under argon atmosphere and stirred for 0.5 hours. The reaction mixture was quenched with water (2 mL), diluted with ethyl acetate (10 mL), washed with water twice (10 mL each) followed by brine (10 mL), dried (Na$_2$SO$_4$), and evaporated. The residue was purified with preparative thin-layer chromatography (silica gel, 2:1 n-hexane/ethyl acetate) to give 14 (54 mg, 87%). 14: pale-brown oil, $^1$H NMR (CDCl$_3$, 400 MHz) δ7.77 (s, 1H), 7.39 (s, 1H), 7.25–7.21 (m, 3H), 6.98–6.96 (m, 2H), 6.28 (s, 1H), 4.50–4.41 (m, 1H), 4.40–4.30 (m, 1H), 4.23 (t, J=7 Hz, 1H), 4.11 (s, 2H), 3.07 (t, J=7.2 Hz, 1H), 2.63 (s, 3H), 1.84–1.6 (m, 2H), 1.43 (s, 6H), 1.4–1.2 (m, 4H), 0.88 (t, J=6.8 Hz, 3H): $^{13}$C NMR (CDCl$_3$, 100 MHz) δ 164.38, 145.18, 138.92, 134.73, 129.75, 129.05, 128.96, 128.68, 126.73, 122.46, 121.32, 111.56, 98.31, 78.71, 67.82, 66.43, 45.18, 36.43, 28.71, 28.48, 22.68, 21.95, 21.52, 14.22: EIHRMS m/z found: 418.2628 (calcd for C$_{27}$H$_{34}$N$_2$O$_2$: 418.2620).

[2-(1-Hydroxypentyl)-5-methyl-1-(2-phenylethyl)]indole-6-carboxylic acid (3). A mixture of 14 (54 mg, 0.13 mmol), acetone (0.5 mL), podomethane (1 mL) and potassium carbonate (54 mg, 0.39 mmol) was stirred at room temperature for 2.5 days, filtered and evaporated. The residue was dissolved with methanol (1 mL), added aqueous sodium hydroxide solution (10%, 0.3 mL) and heated under reflux for 7 hours. The reaction mixture was acidified into pH 6 with hydrochloric acid (1 M), diluted with ethyl acetate (10 mL), washed with brine (10 mL), dried (Na$_2$SO$_4$), and evaporated. The residue was purified with preparative thin-layer chromatography (silica gel, 2:1 n-hexane/ethyl acetate) to give 3 (42 mg, 89%). 3: pale-brown solid, $^1$H NMR (CD$_3$OD, 400 MHz) δ 8.04 (s, 1H), 7.35 (s, 1H), 7.21–7.15 (m, 3H), 7.00–6.89 (m, 2H), 6.30 (s, 1H), 4.45 (t, J=6.8 Hz, 2H), 4.29 (dd, J=2.8 Hz and 5.6 Hz, 1H), 3.11–2.99 (m, 2H), 2.64 (s, 3H), 1.86–1.67 (m, 2H), 1.42–1.18 (m, 4H), 0.92 (t, J=6.8 Hz, 3H): $^{13}$C NMR (CDCl$_3$, 100 MHz) δ 172.98, 147.31, 140.20, 136.08, 132.29, 131.46, 129.99, 129.55, 127.59, 124.50, 123.59, 114.04, 99.29, 66.79, 46.40, 37.43, 36.76, 29.47, 23.64, 22.58, 14.47: EIHRMS m/z found: 365.1986 (calcd for C$_{23}$H$_{27}$NO$_5$: 365.1991).

Ethyl [6-(4,4-dimethyloxazolin-2-yl)-1-ethoxycarbonylmethyl-5-methyl]indole-2-carboxylate (11). To a solution of 6 (449 mg, 1.50 mmol) in DMF (5 mL), sodium hydride (60% suspension in mineral oil, 66 mg, 1.65 mmol) was added at 0° C. under argon atmosphere. After the solution was stirred at 0° C. for 0.5 hours, ethyl bromoacetate (174 microL, 1.58 mmol) was added and stirred for 10 minutes. The reaction mixture was diluted with ethyl acetate (50 mL), washed with water twice (50 mL each) followed by brine (50 mL), dried (Na$_2$SO$_4$), and evaporated. The residue was purified with flash chromatography (silica gel, 3:1 n-hexane/ethyl acetate) to give 11 (428 mg, 74%). 11: pale-yellow solid, $^1$H NMR (CDCl$_3$, 400 MHz) δ 7.76 (s, 1H), 7.50 (s, 1H), 7.26 (s, 1H), 5.27 (s, 2H), 4.32 (quartet, J=7.2 Hz, 2H), 4.20 (quartet, J=7.2 Hz, 2H), 4.10 (s, 2H), 2.61 (s, 3H), 1.41 (s, 6H), 1.38 (t, J=7.2 Hz, 3H), 1.26 (t, J=7.2 Hz, 3H): $^{13}$C NMR (CDCl$_3$, 100 MHz) δ 168.97, 163.53, 162.05, 137.57, 130.64, 129.65, 127.90, 125.59, 124.23, 111.68, 110.32, 78.83, 68.00, 61.60, 60.97, 46.49, 28.62, 21.83, 14.43, 14.26: EIHRMS m/z found: 386.1849 (calcd for C$_{21}$H$_{26}$N$_2$O$_5$: 386.1842).

[[6-(4,4-Dimethyloxazolin-2-yl)-1-(2-hydroxyethyl)-5-methyl]indol-2-yl]methanol (12) was obtained (40 mg, 58%) from 11 (88 mg, 0.23 mmol) by a similar manner as described in a procedure for synthesis of 5 except the oxidation using manganese dioxide was omitted. 12: pale-yellow solid, $^1$H NMR (CD$_3$OD, 400 MHz) δ 7.71 (s, 1H), 7.36 (s, 1H), 6.37 (s, 1H), 4.76 (s, 2H), 4.34 (t, J=5.6 Hz, 2H), 4.18 (s, 2H), 3.86 (t, J=5.6 Hz, 2H), 2.52 (s, 3H), 1.39 (s, 6H): $^{13}$C NMR (CD$_3$OD, 100 MHz) δ 167.63, 143.64, 136.73, 131.42, 129.31, 123.13, 122.16, 112.35, 101.87, 80.14, 68.11, 62.80, 61.96, 57.22, 28.54, 21.30: EIHRMS m/z found: 302.1630 (calcd for C$_{17}$H$_{22}$N$_2$O$_3$: 302.1630).

[6-(4,4-Dimethyloxazolin-2-yl)-1-(2-hydroxyethyl)-5-methyl]indole-2-carboxaldehyde (13a) was obtained (33 mg, 84%) from 12 (40 mg, 0.13 mmol) by a similar manner as described in a procedure for synthesis of 5 except the reduction using lithium aluminum hydride was omitted. 13a: pale-yellow oil, $^1$H NMR (CDCl$_3$, 400 MHz) δ 9.80 (s, 1H), 7.88 (s, 1H), 7.52 (s, 1H), 7.16 (s, 1H), 4.62 (t, J=5.2 Hz, 2H), 4.11 (s, 2H), 3.90 (t, J=5.2 Hz, 2H), 2.58 (s, 3H), 1.40 (s, 6H): $^3$C NMR (CDCl$_3$, 100 MHz) δ 183.23, 163.78, 139.14, 136.93, 130.40, 127.98, 127.21, 124.63, 117.33, 113.05, 79.11, 67.96, 62.39, 47.15, 28.57, 21.60: EIHRMS m/z found: 300.1474 (calcd for C$_{17}$H$_{20}$N$_2$O$_3$: 300.1474).

1-[[6-(4,4-Dimethyloxazolin-2-yl)-1-(2-hydroxyethyl)-5-methyl]indol-2-yl]pentanol (14a) was obtained (28 mg, 72%) from 13a (33 mg, 0.11 mmol) by a similar manner as described in a procedure for synthesis of 14b. 14a: pale-yellow oil, $^1$H NMR (CDCl$_3$, 400 MHz) δ 7.67 (s, 1H), 7.39 (s, 1H), 6.37 (s, 1H), 4.79 (t, J=6.8 Hz, 1H), 4.42–4.37 (m, 1H), 4.34–4.27 (m, 1H), 4.09 (s, 2H), 3.98–3.86 (m, 2H), 2.59 (s, 3H), 2.04–1.95 (m, 2H), 1.6–1.48 (m, 2H), 1.45–1.36 (m, 2H), 1.39 (s, 6H), 0.93 (t, J=7.2 Hz, 3H): $^{13}$C NMR (CDCl$_3$, 100 MHz) δ 165.41, 145.54, 134.84, 130.02, 129.02, 122.55, 121.16, 111.38, 98.64, 79.11, 67.34, 65.38, 60.58, 45.41, 35.14, 28.53, 28.49, 22.90, 21.55, 14.23: EIHRMS m/z found: 358.2259 (calcd for C$_{21}$H$_{30}$N$_2$O$_3$: 358.2256).

[1-(2-hydroxyethyl)-2-(1-Hydroxypentyl)-5-methyl]indole-6-carboxylic acid (2) was obtained (3.3 mg, 65%) from 14a (6.0 mg, 0.017 mmol) by a similar manner as described in a procedure for synthesis of 3. 2: pale-brown amorphous, $^1$H NMR (CD$_3$OD, 400 MHz) δ 8.05 (s, 1H), 7.37 (s, 1H), 6.39 (s, 1H), 4.91 (hidden by solvent peak, supposed as 1H), 4.49–4.42 (m, 1H), 4.40–4.32 (m, 1H), 3.86 (t, J=5.6 Hz, 2H), 2.62 (s, 3H), 2.02–1.95 (m, 2H), 1.6–1.3 (m, 4H), 0.95 (t, J=6.8 Hz, 3H): $^{13}$C NMR (CDCl$_3$, 100 MHz) δ 172.93, 147.64, 136.56, 132.30, 131.55, 126.52, 123.48, 113.99, 99.50, 66.81, 61.93, 46.71, 36.82, 29.52, 23.69, 22.44, 14.42 : EIHRMS m/z found: 305.1627 (calcd for C$_{17}$H$_{23}$NO$_4$: 305.1627).

Methyl(3-amino-4-iodo-6-methyl)benzoate (17). A mixture of 6 (2.0 g, 9.6 mmol) iodomethane (1.2 mL), potassium carbonate (4.0 g) and DMF (10 mL) was stirred at 40° C. for 1 hour. The reaction mixture was diluted with ethyl acetate (100 mL) and washed with water twice (100 mL each) followed by brine (100 mL), dried (Na$_2$SO$_4$), and evaporated to give ester 15. A mixture of 15, methanol (40 mL) and 10% palladium on charcoal (0.1 g) was stirred under hydrogen atmosphere at room temperature for 2 hours. The reaction mixture was filtered and evaporated to give 16 (1.88 g, 2 steps quant.). Iodine monochloride dichloromethane solution (1 M, 13.1 mL) was added to a mixture of 16 (1.58 g), methanol (16 mL), water (1.6 mL), and calcium carbonate (2.45 g) at 0° C. and stirred at room temperature for overnight. The reaction mixture was quenched with a solution of sodium sulfite (1 g) in water (4 mL) at room temperature for 1 hour, filtered and concentrated under reduced pressure. The concentrated solution was diluted with ethyl acetate (700 mL) and washed with water twice (50 mL each) followed by brine (30 mL), dried ($Na_2SO_4$), and evaporated. The residue was purified with flash chromatography (silica gel, 20:1 to 9:1 n-hexane/ethyl acetate) to give 17 (0.81 g, 34%). 17: pale-brown solid. Mp 77° C., $^1$H NMR ($CDCl_3$, 400 MHz) δ 7.53 (s, 1H), 7.29 (s, 1H), 4.04 (s, 2H), 3.86 (s, 3H), 2.42 (s, 3H): $^{13}$C NMR ($CDCl_3$, 100 MHz).

Methyl(2-pentyl-5-methyl)indole-6-carboxylate (19). A mixture of 17 (4.4 mg, 0.015 mmol), 1-heptyne (10 μL), diethylamine (15 μL), dichlorobis(triphenylphosphino)palladium (1.6 mg), copper iodide (0.9 mg) and degassed DMF (60 μL) was stirred at room temperature under argon atmosphere for 2 hours. The reaction mixture was diluted with dichloromethane (2 mL) and purified with preparative thin-layer chromatography (silica gel, 5:1 n-hexane/ethyl acetate) to give methyl[3-amino-4-(hept-1-ynyl)-6-methyl]benzoate 18. 18: pale-yellow amorphous, $^1$H NMR ($CDCl_3$, 400 MHz) δ 7.27 (s, 1H), 7.11 (s, 1H), 4.10 (s, 2H), 3.85 (s, 3H), 2.46 (t, J=7.2 Hz, 2H), 2.42 (s, 3H), 1.63 (quintet, J=7.2 Hz, 2H), 1.44 (quintet, J=7.2 Hz, 2H), 1.37 (quintet, J=7.2 Hz, 2H), 0.92 (t, J=7.2 Hz, 3H). The obtained 18 was dissolved with degassed DMF (80 μL), dichlorobis(benzonitrile)palladium (1.1 mg) was added and stirred at 80° C. under argon atmosphere for 0.5 hours. The reaction mixture was diluted with dichloromethane (2 mL) and purified with preparative thin-layer chromatography (silica gel, 5:1 n-hexane/ethyl acetate) to give 19 (3.4 mg, 87% from 17). 19: brown amorphous, $^1$H NMR ($CDCl_3$, 400 MHz) δ 7.99 (broad s, 1H), 7.98 (s, 1H), 7.34 (s, 1H), 6.18 (s, 1H), 3.89 (s, 3H), 2.75 (t, J=7.2 Hz, 2H), 2.66 (s, 3H), 1.72 (t, J=7.2 Hz, 2H), 1.39–1.34 (m, 4H), 0.90 (t, J=7.2 Hz, 3H): $^{13}$C NMR ($CDCl_3$, 100 MHz).

Methyl[3-formyl-2-pentyl-1-(2-phenylethyl)-5-methyl]indole-6-carboxylate (21). Phosphorous oxychloride (14 μL) was dissolved with dry DMF (0.5 mL) at ice-bath temperature and was kept at the temperature for 0.5 hours under argon atmosphere. The solution was added to a solution of 19 (30 mg, 0.12 mmol) in dry DMF (0.5 mL) at ice-bath temperature and was kept at the temperature for 50 minutes under argon atmosphere. The reaction mixture was diluted with ethyl acetate (20 mL), washed with 10% aqueous sodium bicarbonate solution twice (10 mL each) followed by brine (10 mL), dried ($Na_2SO_4$), and evaporated. The solidified residue was triturated with 5% ethyl acetate/n-hexane and dried to give 20 as a pale-brown solid (33 mg, 99%). Mp 179° C. $^1$H NMR ($CD_3OD$, 400 MHz) δ 10.04 (s, 1H), 8.01 (s, 1H), 7.97 (s, 1H), 3.89 (s, 3H), 3.11 (t, J=8.0 Hz, 3H), 2.65 (s, 3H), 1.86–1.78 (m, 2H), 1.45–1.35 (m, 2H), 0.92 (t, J=7.2 Hz, 3H): $^{13}$C NMR ($CD_3OD$, 100 MHz)

A mixture of 20 (7.1 mg, dry DMF (0.25 mL), 2-bromoethylbenzene (17 μL) and cesium carbonate (16 mg) was stirred at room temperature for 17 hours. Additional 2-bromoethylbenzene (17 μL) and cesium carbonate (64 mg) was added and stirred at room temperature for 2.5 hours. The reaction mixture was diluted with ethyl acetate (20 mL), washed with water followed by brine (10 mL each), dried ($Na_2SO_4$), and evaporated. The residue was purified with preparative thin-layer chromatography (silica gel, 3:1 n-hexane/ethyl acetate) to give 21: pale-yellow amorphous, $^1$H NMR ($CDCl_3$, 400 MHz) δ 10.06 (s, 1H), 8.16 (s, 1H), 7.99 (s, 1H), 7.26–7.22 (m, 3H), 6.98–6.94 (m, 2H), 4.36 (t, J=6.8 Hz, 2H), 3.95 (s, 3H), 3.11 (t, J=7.2 Hz, 2H), 2.72 (s, 3H), 2.66 (t, J=8.0 Hz, 2H), 1.59–1.50 (m, 2H), 1.34–1.25 (m, 4H), 0.88 (t, J=6.4 Hz, 3H): $^{13}$C NMR ($CDCl_3$, 100 MHz) δ 168.60, 154.87, 137.64, 135.00, 134.18, 129.09, 128.94, 127.39, 124.61, 123.58, 119.13, 113.53, 112.92, 52.05, 45.49, 36.18, 31.77, 30.27, 29.90, 24.33, 22.43, 14.07. ESI-HRMS calcd.; 391.2147 found; 391.2144.

Sodium[3-hydroxymethyl-2-(1-pentyl)-1-(2-phenylethyl)-5-methyl]indole-6-carboxylate (4). A solution of 21 (4.5 mg, 0.011 mmol) of methanol (0.5 mL) was treated with sodium borohydride (1 mg). The reaction mixture was quenched with water (2 mL), diluted with ethyl acetate (10 mL), washed with water twice (10 mL each) followed by brine (10 mL), dried ($Na_2SO_4$), and evaporated to give methyl[3-hydroxymethyl-2-(1-pentyl)-1-(2-phenylethyl)-5-methyl]indole-6-carboxylate 22 as a pale-brown amorphous. 22: $^1$H NMR ($CDCl_3$, 400 MHz) δ 7.99 (s, 1H), 7.49 (s, 1H), 7.30–7.22 (m, 3H), 7.06 (d, J=6.8 Hz, 2H), 4.77 (s, 2H), 4.31 (t, J=7.6 Hz, 2H), 3.93 (s, 3H), 3.04 (t, J=7.6 Hz, 2H), 2.70 (s, 3H), 2.54 (t, J=7.6 Hz, 2H), 1.56–1.47 (m, 2H), 1.36–1.22 (m, 4H), 0.88 (t, J=6.8 Hz, 3H): $^{13}$C NMR ($CDCl_3$, 100 MHz) δ 169.11, 143.48, 138.43, 133.88, 131.52, 130.85, 128.96, 128.89, 127.05, 122.47, 120.49, 112.77, 111.05, 55.95, 51.83, 45.37, 36.78, 31.90, 30.31, 24.52, 22.62, 22.58, 14.16. HRMS: calcd. 393.2304 found; 393.2314. The obtained 22 was treated with sodium hydroxide (aqueous 5% solution, 33 μL) in methanol (0.1 mL) at 60° C. for 22 h, evaporated and pumped-up to afford 4 (11 mg). 4: white powder, $^1$H NMR ($CD_3OD$, 400 MHz) δ 7.64 (s, 1H), 7.40 (s, 1H), 7.26–7.19 (m, 3H), 7.09 (d, J=7.2 Hz, 2H), 4.69 (s, 2H), 4.30 (t, J=7.2 Hz, 2H), 3.04 (t, J=7.2 Hz, 2H), 2.60 (s, 3H), 2.52 (t, J=7.6 Hz, 2H), 1.54–1.46 (m, 2H), 1.36–1.28 (m, 4H), 0.90 (t, J=6.4 Hz, 3H): $^{13}$C NMR ($CD_3OD$, 100 MHz) δ 168.14, 141.81, 140.24, 135.15, 135.05, 129.96, 129.70, 129.60, 127.88, 127.60, 120.30, 111.25, 110.13, 55.76, 46.27, 37.34, 32.91, 31.19, 24.24, 23.45, 21.38, 14.38. ESI-HRMS: calcd.; 362.2115 (M–OH)$^+$. found; 362.2120 (M–OH)$^+$.

Protein Expression

A plasmid consisting of a GST fusion construct of the second PDZ domain of MAGI-3 was obtained from Genentech. The plasmid was transformed into BL21 DE3 cells, grown at 37° C. to an O.D.$_{600}$ of 0.8, and induced with 1 mM of IPTG. After three hours the cells were harvested, lysed, and the protein was purified through a slurry of glutathione sepharose beads (Pharmacia). The protein was dialyzed into the assay buffer (35 mM HEPES at pH 7.4, 0.01% triton X-100, 10% glycerol) and concentrated with 10,000 MW cutoff Centricon filters (Waters). Protein purity was verified by SDS-PAGE with Coomassie and silver staining. Quantification of the protein was done with the BCA protocol by Pierce. The protein was stored in the assay buffer at –80° C. GST alone was expressed, purified and stored in the same manner.

Binding Assay

A fluorescence polarization competition assay was used to detect binding of the compounds to MAGI-3 PDZ2. A fluorescein labeled carboxy terminal sequence of PTEN, OregonGreen™-PFDEDQHTQITKV-COOH (SEQ ID NO:1), was used as a probe. For a positive control, we chose PFDEDQHTQITWV-COOH (SEQ ID NO:2), the highest affinity peptide sequence for MAGI-3 PDZ2 known. To synthesize the labeled peptide we used standard Fmoc conditions on Wang resin to build a 13 residue peptide. A typical coupling cycle includes deprotecting the terminal amino acid with 20% piperidine in dry DMF, washing the resin 2–3 times with DMF then methylene chloride and both again, and determining the existence of free amine by ninhydrin kaiser test. A slurry containing coupling reagent 2.4 equivalents of HBTU, the next N terminal amino acid to be added to the growing peptide 2.5 equivalents of Fmoc protected amino acid, 5 equivalents of DIEA in dry DMF. The amino acid was coupled over 2–3 hours and the kaiser test was used to determine completeness. Coupling steps were repeated if a positive kaiser test resulted. This method was used for each residue of the peptide. The finished peptide was cleaved from the resin with 95% TFA with a cocktail of scavengers including thioanisole and phenol. The peptide was precipitated with ether and lyophilyzed. Peptides were purified using HPLC and identified with MALDI mass spectrometry.

To detect binding of compounds to the PDZ2 domain of the MAGI-3 protein, a competition polarization assay was employed. The buffer included 35 MM HEPES at pH 7.4, triton X-100 0.01%, and 10% glycerol. The protein was added to a final concentration of 300 nM and the probe, 10 nM. The competitor was then added to final concentration range of 10 pM to 300 µM. Triplicates of the samples in a total volume of 20 µL were transferred to 384 well Corning opaque plate for analysis. Fluorescence polarization was measured at equilibrium by LJL Biosystems plate reader. Competition data was fit to a one-site competition expression and the $IC_{50}$ values of the nonpeptide compounds were compared.

Figure 2:
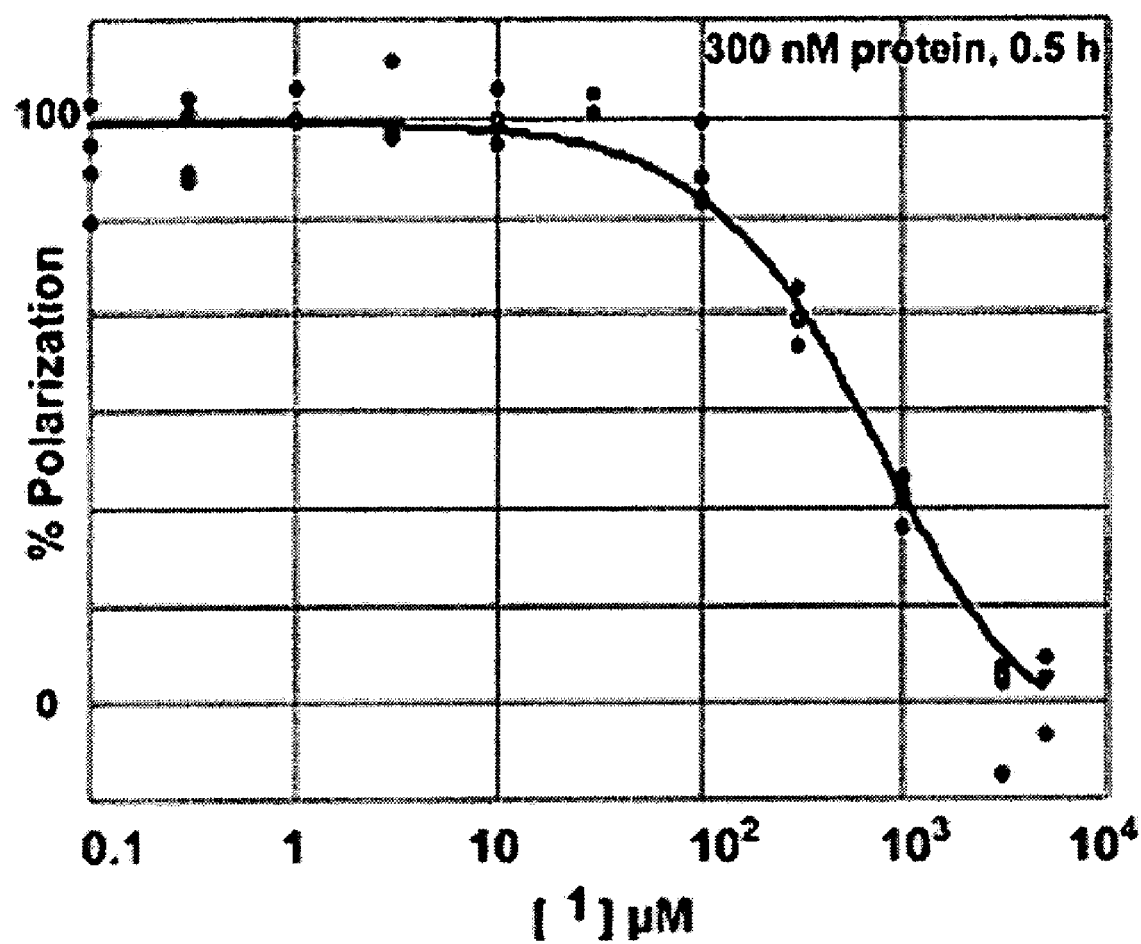
FIG. 2 depicts fluorescence polarization competition of a compound of the invention for the PDZ2 binding site on protein GST-MAGI-3.

FIG. 2 shows the fluorescence polarization competition of inhibitor 3 (above) (Table I, compound 1) for the binding site of OG-PFDEDQHTQITTV-COOH (SEQ ID NO:3) (10 nM) on GST-MAGI-3 PDZ2 (300 nM).

Figure 3:
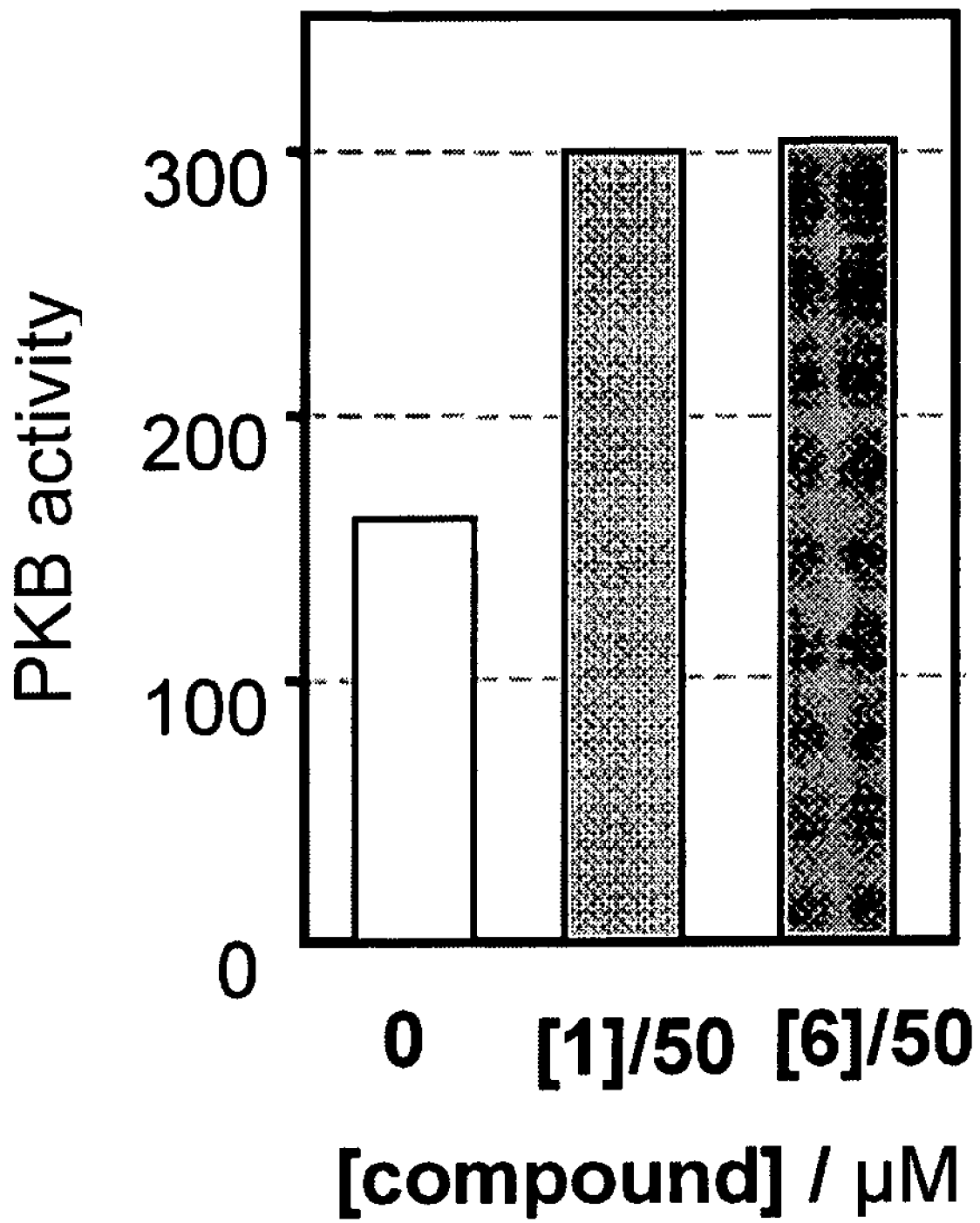
FIG. 3 depicts the effect of two compounds of the invention on PKB activity.

FIG. 3 shows the results of this test: the effect of PDZ inhibitors 2 and 4 (above) (Table I, compound 1; Table II compound 6, respectively) on PKB activity.

Figure 4:
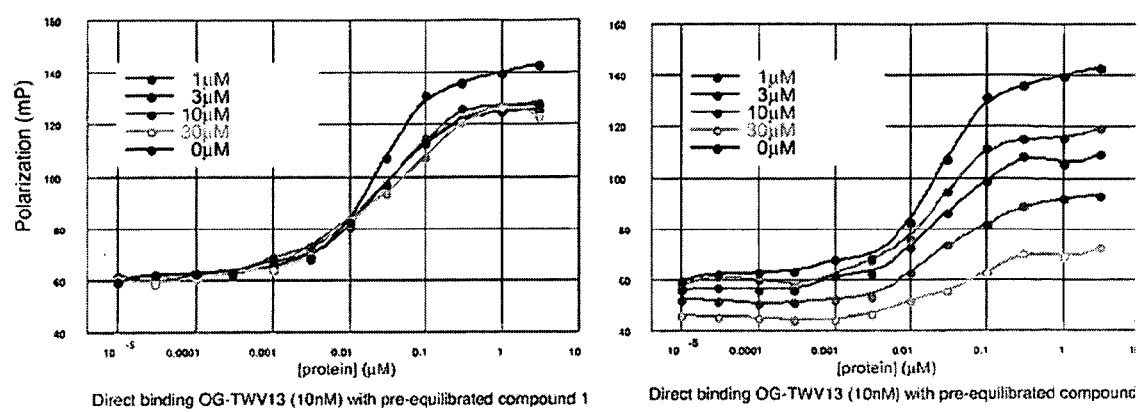
FIG. 4 depicts the results of an evaluation of the irreversible character of a compound of the invention.

FIG. 4 shows the results of an evaluation of the irreversible character of the binding of inhibitor 4 (Table 2, compound 6) to the MAGI3 PDZ2 domain Antibodies Anti-phospho-Ser473 for immunoblotting were produced by injecting rabbits with the peptides CRPHFPQFS(P) YSASGT (SEQ ID NO:4), and antibodies recognizing unphosphorylated peptide were removed by binding to non-phosphopeptide columns. The unbound material was then affinity purified over a phosphopeptide column. The antibodies used for PKB immunoprecipitation (IP) kinase assays were generated by injecting rabbits with recombinant full-length PKB. Polyclonal anti-SHIP-2 antibody was generated by immunizing rabbits with glutathione S-transferase fused to the C-terminal region of SHIP-2. Anti-PKB kinase (i.e., PDK-1) was purchased from Transduction Laboratories. Horseradish peroxidase-conjugated secondary antibodies were obtained from Amersham-Pharmacia.

Immunoprecipitation and In Vitro PKB Assay

Subconfluent monolayers of HCT116 cells were lysed by scraping the cells into lysis buffer (20 mM Tris-HCl, pH 7.5, containing 1% NP-40, 1 mM EGTA, 1 mM EDTA, 1 mM sodium orthovanadate, and protease inhibitor cocktail [Boehringer Mannheim]) at 4° C. After centrifugation (10,000 ×g for 10 min at 40° C.) to remove insoluble components, endogenous PKB was immunoprecipitated (IPed) using the anti-PKB antibody and protein A-Sepharose at 40° C. for 1 h. After washing the IP, kinase activity was assayed using the synthetic peptide GRPRTSSFAEG (SEQ ID NO:5) (Crosstide) as a substrate in a reaction mixture containing 20 mM Tris-HCl (pH 7.5), 75 mM NaCl, 10 mM $MgCl_2$, 1 mM dithiothreitol (DTT), 20 µM ATP, 50 µM Crosstide, and 5 µCi of $[-^{32}P]$ATP in a volume of 20 µl per assay. The reaction was allowed to proceed for 15 min at 30° C. and then was stopped by spotting 18 µl onto Whatman P81 filter papers and immersing them in 1% (vol/vol) orthophosphoric acid. The papers were washed four times, rinsed once in acetone, and air dried, and the radioactivity was determined by scintillation counting. Alternatively, the phosphorylation reactions were stopped by the addition of Tricine sample buffer, the phosphopeptide was separated on a 16% Tricine gel, and the amount of $^{32}P$ radioactivity was assessed using a STORM PhosphorImager (Molecular Dynamics).

Apoptotic Effects of Compounds in Cancer Cells Overexpressing Dvl

Compounds were tested for apoptotic effects to represent the inhibitory effects of compounds on interaction between the PDZ domain of the Dishevelled (Dlv) protein and the Fz protein (Wnt receptor). Cell lines H513 and H1703 were utilized, with test compounds (compound numbers from Tables 1 and 2) being applied at 0 (control), 10 µM and 100 µM. Results were as follows:

| Compound no. | Conc., µM | Cell line | days | apoptosis, % |
|---|---|---|---|---|
| 1 | 10 | H1703 | 4 | 6.2 |
| 1 | 100 | H1703 | 4 | 38.7 |
| 6 | 10 | H1703 | 1 | 8.2 |
| 6 | 100 | H1703 | 1 | 34.0 |
| 6 | 10 | H513 | 1 | 14.3 |
| 6 | 100 | H513 | 1 | 52.5 |

In other tests, Compound 6 (Table II) was found to bind human Dishevelled (Dvl) protein; and at 100 µM, and after 4 days, was also found to suppress cancer cell growth and induce apoptosis in up to 85.2% of the population in human lung cancer (H1073) cells;

over 50% of the population in human mesothelioma (H513) cells;

35% of the population in human melanoma (LOX) cells;

about 20% of the population in human lung cancer (H460) cells;

and to inhibit Wnt/beta-Catenin signaling in human lung cancer cell lines A549 and H1703.

Other proteins that are targets of the compounds of this invention, particularly for anti-tumor activity, include NHREF-1/EPB50, ZO-1, NNOS, ERBIN and MUPP1.

It is understood that the examples and embodiments described herein are for illustrative purposes only and that various modifications or changes in light thereof will be suggested to persons skilled in the art and are to be included within the spirit and purview of this application and scope of the appended claims.

All publications, patents, and patent applications cited herein are hereby incorporated by reference in their entirety for all purposes.

What is claimed is:

1. A compound having the formula

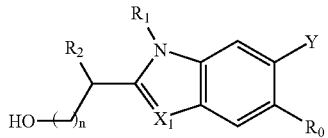

in which:

$R_0$ is selected from the group consisting of $C_1$–$C_3$ alkyl, cyclopropyl, halo, $OR_5$ and $S(O)_m R_5$ in which m is 0, 1 or 2;

$R_1$ and $R_2$ are independently selected from the group consisting of $C_2$–$C_8$ alkenyl, phenylcyclopropyl, phenylpropenyl, $R_6$—$X_2$—$C(R_8)(R_8)$—$R_7$—; and $R_6$—$X_2$—$N(R_8)$—$R_7$—;

or $R_2$ is $(CH_2)_m C_6 H_5$ wherein m' is 0 or an integer from 1 to 3, or $R_2$ is $C_3$–$C_6$ cycloalkyl;

$R_3$ and $R_4$ are independently hydrogen, methyl or ethyl;

$R_5$ is methyl or ethyl;

$R_6$ is selected from the group consisting of hydrogen, $C_1$–$C_{10}$ alkyl, aryl, W, Y, $NH_2$, $NHCONR_3R_4$, $NHCOOR_3$ and $NHSO_2R_9$;

$R_7$ is selected from the group consisting of a direct bond, an alkyl group having from 1 to 10 carbon atoms, aryl, —$(NH)_p(CH_2CH_2O)_q(NH)_p$— in which p is 0 or 1 and q is an integer from 1 to 4, and W;

$R_8$ is selected from the group consisting of H, Y, OH, —$NHCONR_3R_4$; —$NHCOOR_3$; —$NHSO_2R_9$, —$(CH_2)_r CO_2 R_3$, and $(CH_2)_r CO_2 NR_3 R_4$ in which r is an integer from 1 to 3;

$R_9$ is aryl or $C_1$–$C_6$ alkyl;

$X_1$ is —CH—, —C-hal, —$C(CH_3)$ or —$C(C_2H_5)$, in which hal stands for a halogen atom (preferably chloro, fluoro or bromo);

$X_2$ is selected from the group consisting of a direct bond, —NH—, —$N(CH_3)$—, —$NCONR_3R_4$—, —$NCOOR_3$—, and $NSO_2R_9$;

W is a saturated carbocyclic or heterocyclic group;

Y is selected from the group consisting of COOH, $COOR_3$, $CONR_3R_4$, $CONHSO_2R_5$, hydroxymethyl, —$CH_2COOH$, $CH_2CONR_3R_4$; and 5-tetrazolyl; and n is zero hydrates and salts thereof, and labeled derivatives thereof.

2. A compound according to claim 1 in which Y is COOH or $COOR_3$.

3. A compound according to claim 1 in which $R_0$ is a $C_1$–$C_3$ alkyl group.

4. A compound according to claim 3 in which $R_0$ is methyl.

5. A compound according to claim 1 in which $R_1$ is optionally substituted phenethyl.

6. A compound according to claim 1 in which $R_1$ is 2-hydroxyethyl.

7. A compound according to claim 1 in which $R_2$ is n-butyl, phenyl or 1-hydroxy-n-butyrylamido.

8. A compound according to claim 1 in which $R_2$ is $R_6$—$X_2$—$C(R_8)(R_8)$—$R_7$— or $R_6$—$X_2$—$N(R_8)$—$R_7$—, and the group $R_6$—$X_2$—$C(R_8)(R_8)$—$R_7$— or $R_6$—$X_2$—$N(R_8)$—$R_7$— is selected from $C_3$–$C_8$ alkyl; $C_3$–$C_6$ cycloalkyl; $C_3$–$C_8$ alkenyl; $(CH_2)_{m'} C_6 H_5$ where m' is 0 or an integer from 1–3; —$CH_2OC_6H_5$, $CH_2COC_6H_5$, phenyl($C_2$–$C_4$ alkenyl), or analogous moieties having substituted phenyl groups; optionally substituted phenylcyclopropyl; —$(CH_2)_s$OH, —$(CH_2)_s CONH_2$ and —$(CH_2)_s COOH$ where s is an integer from 1 to 3; phenyl; thienyl; and optionally substituted $C_3$–$C_6$ cycloalkyl-($C_1$–$C_3$ alkyl).

9. A compound according to claim 1 in which $R_0$ is methyl, $R_1$ is phenethyl, $R_2$ is n-butyl, $X_1$ is —CH, Y is COOH and n is 0.

10. A compound according to claim 1 in which $R_0$ is methyl, $R_1$ is 2-hydroxyethyl, $R_2$ is n-butyl, $X_1$ is —CH, Y is COOH and n is 0.

11. A compound according to claim 1 in which $R_2$ is phenethyl or 2-hydroxyethyl.

12. A compound according to claim 1 in which $R_1$ is $C_3$–$C_8$ alkyl.

13. A compound according to claim 1 in which $R_0$ is methyl, $R_1$ is n-pentyl, $R_2$ is phenethyl, $X_1$ is —CH and Y is COOH.

14. A probe comprising a compound according to claim 1 and a detectable label.

15. A combinatorial library of two or more compounds having the formula

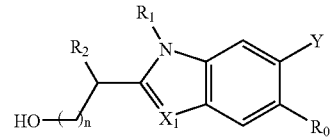

in which:

$R_0$ is selected from the group consisting of $C_1$–$C_3$ alkyl, cyclopropyl, halo, $OR_5$ and $S(O)_m R_5$ in which m is 0, 1 or 2;

$R_1$ and $R_2$ are independently selected from the group consisting of $C_2$–$C_8$ alkenyl, phenylcyclopropyl, phenylpropenyl,), $R_6$—$X_2$—$C(R_8)(R_8)$—$R_7$—; and $R_6$—$X_2$—$N(R_8)$—$R_7$—; or $R_2$ is phenyl;

$R_3$ and $R_4$ are independently hydrogen, methyl or ethyl;

$R_5$ is methyl or ethyl;

$R_6$ is selected from the group consisting of hydrogen, $C_1$–$C_{10}$ alkyl, aryl, W, Y, $NH_2$, $NHCONR_3R_4$, $NHCOOR_3$ and $NHSO_2R_9$;

$R_7$ is selected from the group consisting of a direct bond, an alkyl group having from 1 to 10 carbon atoms, aryl, —$(NH)_p(CH_2CH_2O)_q(NH)_p$— in which p is 0 or 1 and q is an integer from 1 to 4, and W;

$R_8$ is selected from the group consisting of H, Y, OH, —$NHCONR_3R_4$; —$NHCOOR_3$; —$NHSO_2R_9$, —$(CH_2)_rCO_2R_3$, and $(CH_2)_rCO_2NR_3R_4$ in which r is an integer from 1 to 3;

$R_9$ is aryl or $C_1$–$C_6$ alkyl;

$X_1$ is —CH—, —C-hal, —$C(CH_3)$ or —$C(C_2H_5)$, in which hal stands for a halogen atom (preferably chloro, fluoro or bromo);

$X_2$ is selected from the group consisting of a direct bond, —NH—, —$N(CH_3)$—, —$NCONR_3R_4$—, —$NCOOR_3$—, and $NSO_2R_9$;

W is a saturated carbocyclic or heterocyclic group;

Y is selected from the group consisting of COOH, $COOR_3$, $CONR_3R_4$, $CONHSO_2R_5$, hydroxymethyl, —$CH_2COOH$, $CH_2CONR_3R_4$; and 5-tetrazolyl; and n is zero and hydrates and salts thereof, and labeled derivatives thereof.

16. A method for treating a cancer selected from the group consisting of human lung cancer, human mesothelioma and human melanoma in cancerous cells or in a patient comprising contacting the cancerous cells with, or administering to the patient, a therapeutically effective amount of a compound according to claim 1.

17. A method for treating a cancer selected from the group consisting of human lung cancer, human mesothelioma and human melanoma in cancerous cells or in a patient comprising contacting the cancerous cells with, or administering to the patient a therapeutically effective amount of a compound according to claim 7.

18. A method for treating a cancer selected from the group consisting of human lung cancer, human mesothelioma and human melanoma in cancerous cells or in a patient comprising contacting the cancerous cells with, or administering to the patient a therapeutically effective amount of a compound according to claim 12.

* * * * *

UNITED STATES PATENT AND TRADEMARK OFFICE
CERTIFICATE OF CORRECTION

PATENT NO. : 7,141,600 B2
APPLICATION NO. : 10/826175
DATED : November 28, 2006
INVENTOR(S) : R. Kiplin Guy et al.

Page 1 of 1

It is certified that error appears in the above-identified patent and that said Letters Patent is hereby corrected as shown below:

In claim 15, column 34, line 64:

change "nylpropenyl,)," to --nylpropenyl,--

In claim 15, column 36, line 1:

change "hydrates and salts thereof," to --hydrates, salts thereof--

In claim 17, column 36, line 15:

change "claim 7" to --claim 9--

In claim 18, column 36, line 21:

change "claim 12" to --claim 13--

Signed and Sealed this

Twenty-ninth Day of May, 2007

JON W. DUDAS
*Director of the United States Patent and Trademark Office*